United States Patent
Kim et al.

(10) Patent No.: US 10,101,655 B2
(45) Date of Patent: *Oct. 16, 2018

(54) COMPOUND, POLYMER, PHOTOSENSITIVE RESIN COMPOSITION, AND COLOR FILTER

(71) Applicant: SAMSUNG SDI CO., LTD., Yongin-si, Gyeonggi-do (KR)

(72) Inventors: Kyuyoung Kim, Suwon-si (KR); Hyeongmook Kim, Suwon-si (KR); Young Lee, Suwon-si (KR); Myoungyoup Shin, Suwon-si (KR); Seungjib Choi, Suwon-si (KR)

(73) Assignee: SAMSUNG SDI CO., LTD., Yongin-si, Gyeonggi-do (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/404,689

(22) Filed: Jan. 12, 2017

(65) Prior Publication Data

US 2017/0248846 A1 Aug. 31, 2017

(30) Foreign Application Priority Data

Feb. 26, 2016 (KR) .................. 10-2016-0023627
Oct. 12, 2016 (KR) .................. 10-2016-0132197

(51) Int. Cl.

| | |
|---|---|
| *G02B 5/20* | (2006.01) |
| *G03F 7/016* | (2006.01) |
| *G03F 7/021* | (2006.01) |
| *C08F 220/68* | (2006.01) |
| *C09B 11/24* | (2006.01) |
| *G02B 5/22* | (2006.01) |
| *C09B 69/10* | (2006.01) |
| *C07D 311/82* | (2006.01) |
| *G03F 7/00* | (2006.01) |

(52) U.S. Cl.
CPC .......... *G03F 7/0163* (2013.01); *C07D 311/82* (2013.01); *C08F 220/68* (2013.01); *C09B 11/24* (2013.01); *C09B 69/109* (2013.01); *G02B 5/223* (2013.01); *G03F 7/0007* (2013.01); *G03F 7/021* (2013.01)

(58) Field of Classification Search
CPC ..... C07D 311/82; G03F 7/0007; G03F 7/028; G03F 7/033; G02B 5/223; C09B 69/109
See application file for complete search history.

(56) References Cited

U.S. PATENT DOCUMENTS

2006/0020141 A1 1/2006 Banning et al.

FOREIGN PATENT DOCUMENTS

| JP | 4287030 B2 | 7/2009 |
|---|---|---|
| JP | 2012-032754 A | 2/2012 |
| JP | 2012-230365 A | 11/2012 |
| JP | 2013-047285 A | 3/2013 |
| JP | 2013-050707 A | 3/2013 |
| JP | 2013-064099 A | 4/2013 |
| JP | 2013-100463 A | 5/2013 |
| JP | 2013-163804 A | 8/2013 |
| JP | 2014-012814 A | 1/2014 |
| JP | 2015-143330 A | 8/2015 |
| JP | 2015-145439 A | 8/2015 |
| JP | 2016-060828 A | 4/2016 |
| JP | 2016-065219 A | 4/2016 |
| JP | 2016-065220 A | 4/2016 |
| JP | 2016-069656 A | 5/2016 |
| JP | 2016-118619 A | 6/2016 |
| KR | 10-1367572 B1 | 3/2014 |
| KR | 10-2015-0116441 a | 10/2015 |
| KR | 10-2016-0025612 A | 3/2016 |
| KR | 10-2016-0056294 A | 5/2016 |

OTHER PUBLICATIONS

Computer-generated translation of JP 2016-065220 (Apr. 2016).*
Computer-generated translation of JP 2016-065219 (Apr. 2016).*
Provisional double patenting rejection over claims of the above-identified application; USPTO Office action dated Dec. 7, 2017, in U.S. Appl. No. 15/372,430.

* cited by examiner

*Primary Examiner* — John A McPherson

(74) *Attorney, Agent, or Firm* — Lee & Morse, P.C.

(57) ABSTRACT

A compound, an acrylic polymer formed by a copolymerization reaction of the compound with an ethylenic unsaturated monomer, photosensitive resin composition including the compound being represented by Chemical Formula 1 and a color filter:

[Chemical Formula 1]

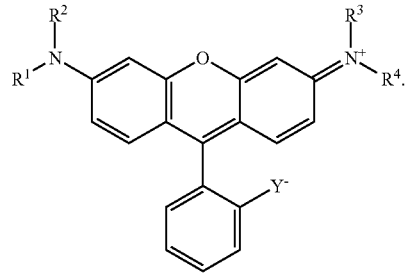

27 Claims, No Drawings

COMPOUND, POLYMER, PHOTOSENSITIVE RESIN COMPOSITION, AND COLOR FILTER

CROSS-REFERENCE TO RELATED APPLICATIONS

Korean Patent Application Nos. 10-2016-0023627, filed on Feb. 26, 2016, and 10-2016-0132197, filed on Oct. 12, 2016, in the Korean Intellectual Property Office, and entitled: "Novel Compound, Novel Polymer, Colorant Including the Same, Positive Photosensitive Resin Composition Including the Same, and Color Filter," are incorporated by reference herein in its entirety.

BACKGROUND

1. Field

Embodiments relate to a compound, a polymer, a colorant including the same, a photosensitive resin composition including the same, and a color filter.

2. Description of the Related Art

A liquid crystal display device among many kinds of displays has an advantage of lightness, thinness, low cost, low power consumption for operation, and improved adherence to an integrated circuit and has been widely used for a laptop computer, a monitor, and a TV screen. The liquid crystal display device may include a lower substrate on which a black matrix, a color filter, and an ITO pixel electrode are formed, and an upper substrate on which an active circuit portion including a liquid crystal layer, a thin film transistor, and a capacitor layer and an ITO pixel electrode are formed. Color filters may be formed in a pixel region by sequentially stacking a plurality of color filters (e.g., formed of three primary colors such as red (R), green (G), and blue (B)) in a predetermined order to form each pixel, and a black matrix layer may be disposed in a predetermined pattern on a transparent substrate to form a boundary between the pixels.

SUMMARY

Embodiments are directed to a compound, a polymer, a colorant including the same, a photosensitive resin composition including the same, and a color filter.

The embodiments may be realized by providing a compound represented by Chemical Formula 1:

[Chemical Formula 1]

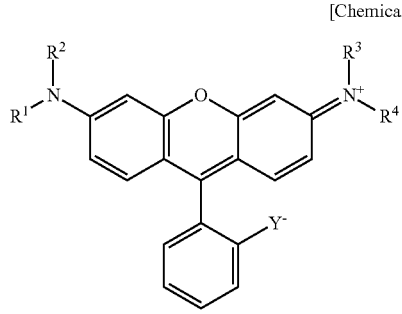

wherein, in Chemical Formula 1, $R^1$ to $R^4$ are each independently a hydrogen, a substituted or unsubstituted C1 to C20 alkyl group, a substituted or unsubstituted C2 to C20 alkenyl group, a substituted or unsubstituted C3 to C20 cycloalkyl group, a substituted or unsubstituted C6 to C20 aryl group, a substituted or unsubstituted C2 to C20 heteroaryl group or a group represented by Chemical Formula 2, at least one of $R^1$ to $R^4$ being a group represented by Chemical Formula 2,

[Chemical Formula 2]

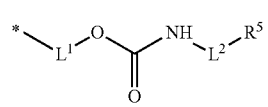

wherein, in Chemical Formula 2, $L^1$ is a substituted or unsubstituted C1 to C20 alkylene group, $L^2$ is a single bond, a substituted or unsubstituted C1 to C20 alkylene group, a substituted or unsubstituted C3 to C20 cycloalkylene group, or a substituted or unsubstituted C6 to C20 arylene group, $R^5$ is a substituted or unsubstituted C3 to C20 cycloalkyl group or a substituent including an ethylenic unsaturated double bond, and Y is *—$SO_3$ or *—$SO_2NSO_2CF_3$, and wherein * is a bonding site.

$R^5$ may be the substituted or unsubstituted C3 to C20 cycloalkyl group, a substituted or unsubstituted acrylate group, a substituted or unsubstituted C2 to C20 alkenyl group, or a C6 to C20 aryl group including a substituent having an ethylenic unsaturated double bond at a terminal end thereof.

$R^5$ may be an unsubstituted cyclohexyl group or a substituent represented by one of the following Chemical Formula 3 to Chemical Formula 5:

[Chemical Formula 3]

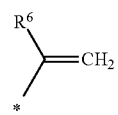

[Chemical Formula 4]

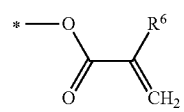

[Chemical Formula 5]

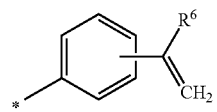

wherein, in Chemical Formulae 3 to 5, $R^6$ may be a hydrogen atom or a substituted or unsubstituted C1 to C5 alkyl group, and * is a bonding site.

At least two of $R^1$ to $R^4$ may be groups represented by Chemical Formula 2.

$R^1$ or $R^2$ may be a group represented by Chemical Formula 2.

$R^3$ or $R^4$ may be a group represented by Chemical Formula 2.

The compound represented by Chemical Formula 1 may be a compound represented by one of Chemical Formula 6-1 to 17-2:

[Chemical Formula 6-1]
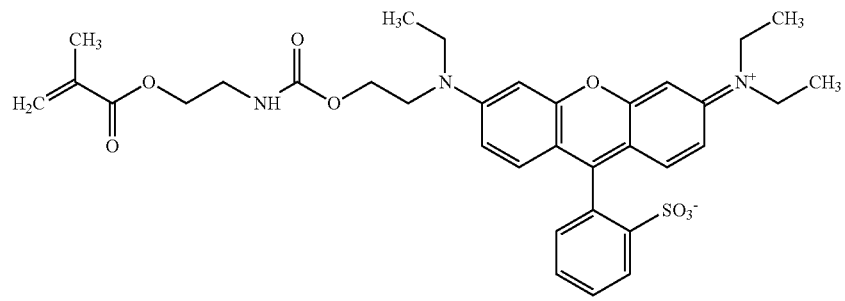
[Chemical Formula 6-2]
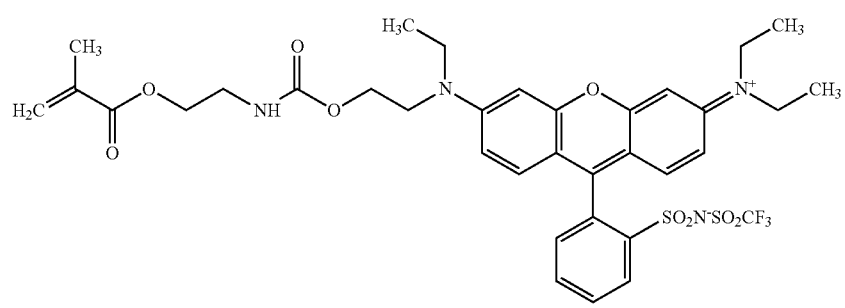
[Chemical Formula 7-1]
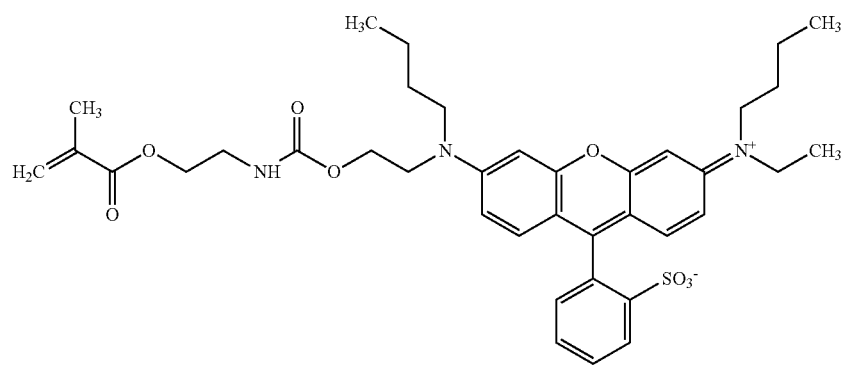
[Chemical Formula 7-2]
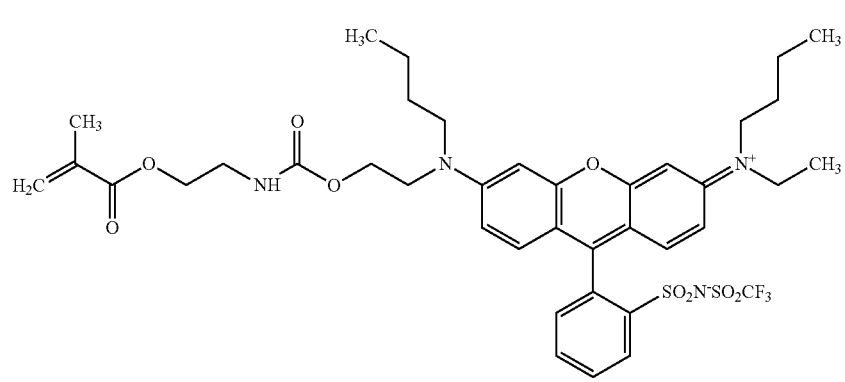

-continued
[Chemical Formula 8-1]
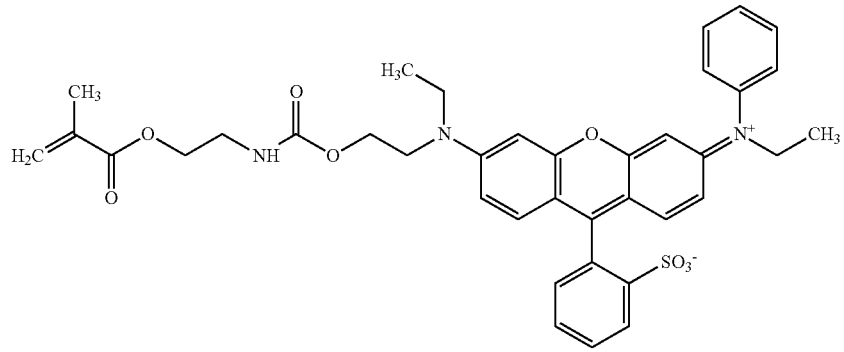
[Chemical Formula 8-2]
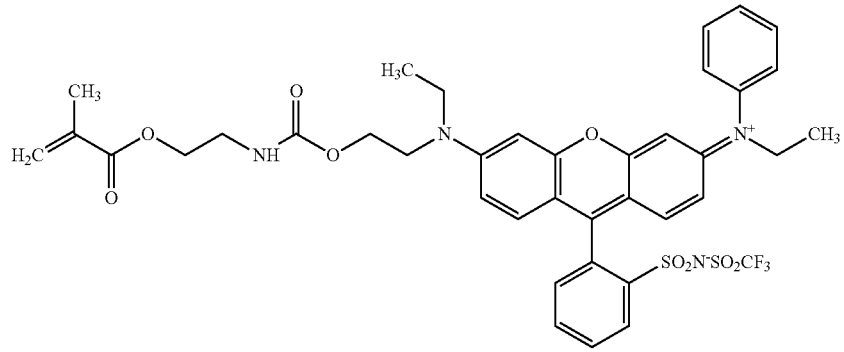
[Chemical Formula 9-1]
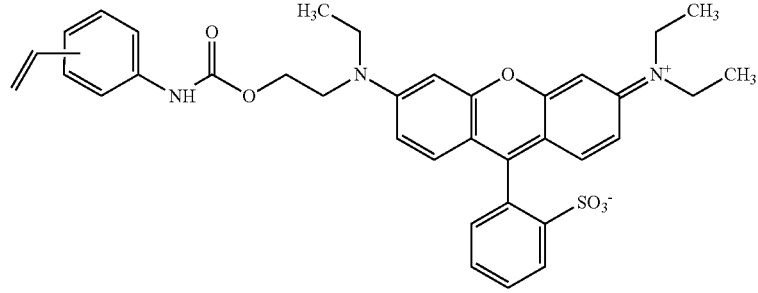
[Chemical Formula 9-2]
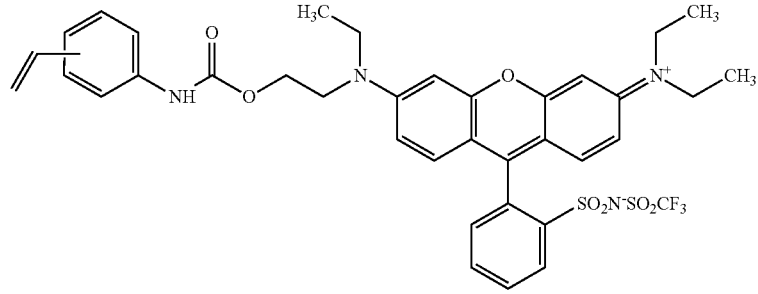
[Chemical Formula 10-1]
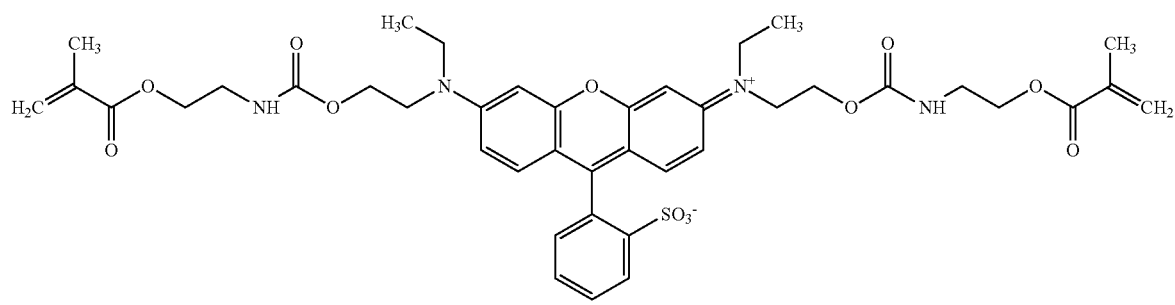

[Chemical Formula 10-2]
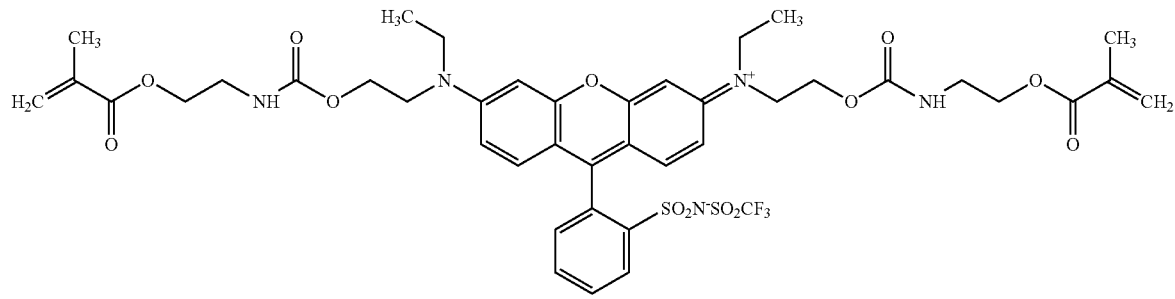
[Chemical Formula 11-1]
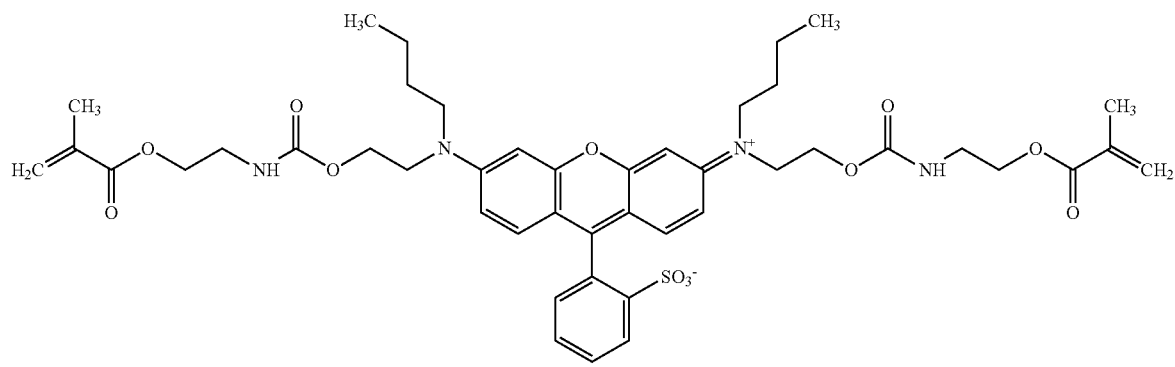
[Chemical Formula 11-2]
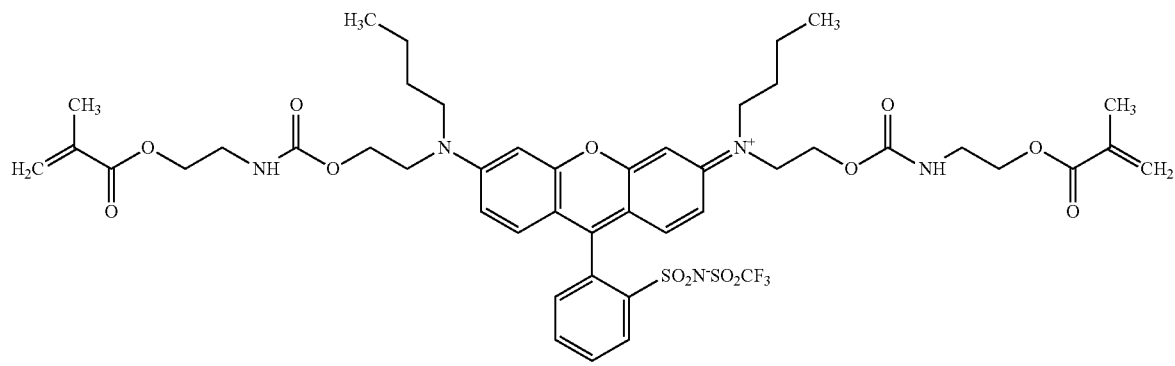
[Chemical Formula 12-1]
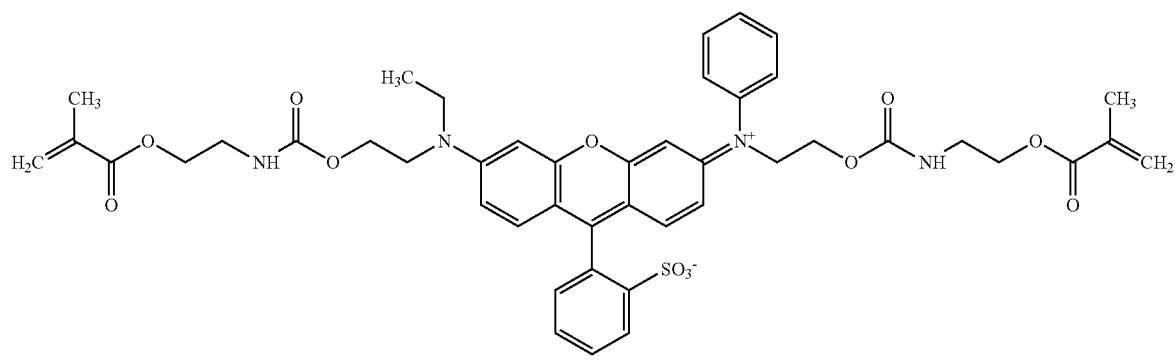

-continued
[Chemical Formula 12-2]
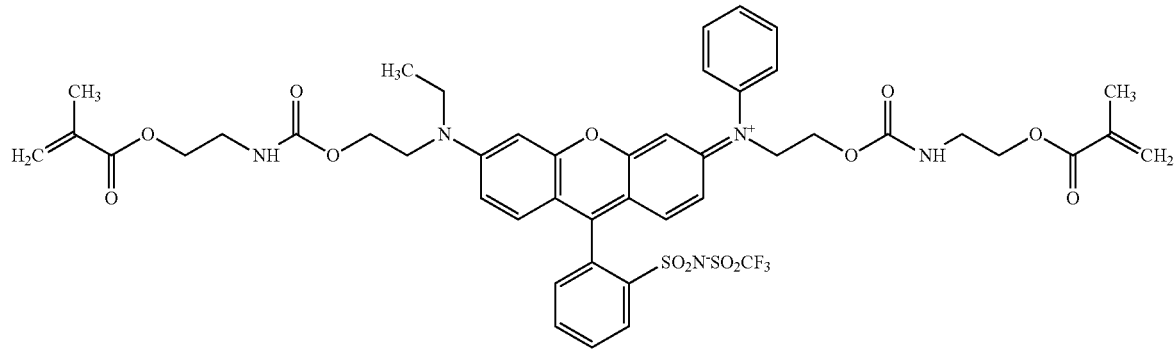
[Chemical Formula 13-1]
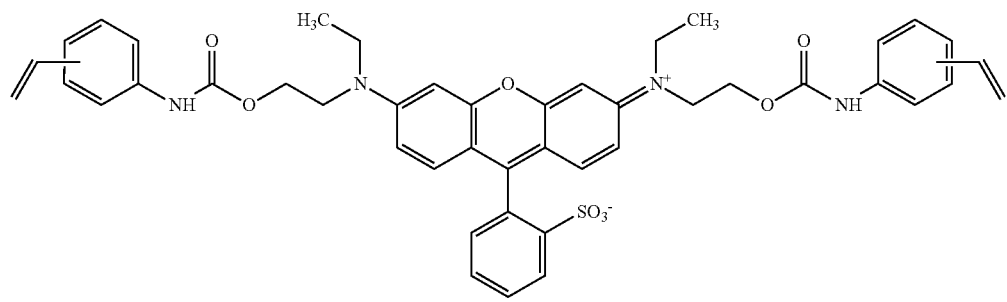
[Chemical Formula 13-2]
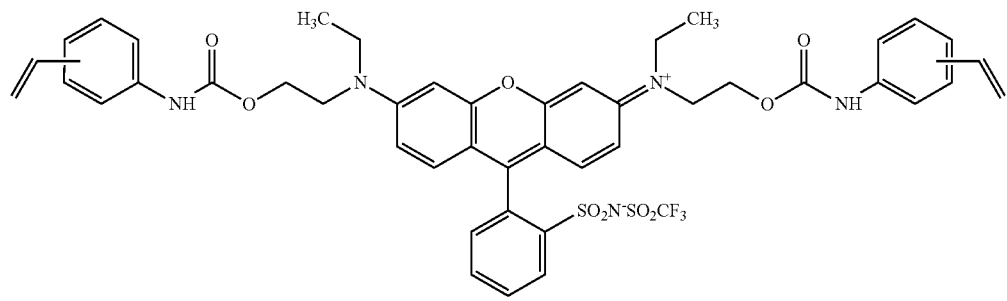
[Chemical Formula 14-1]
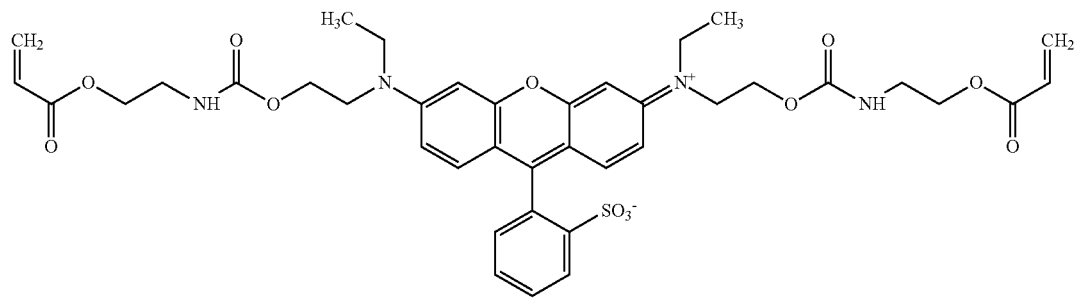
[Chemical Formula 14-2]
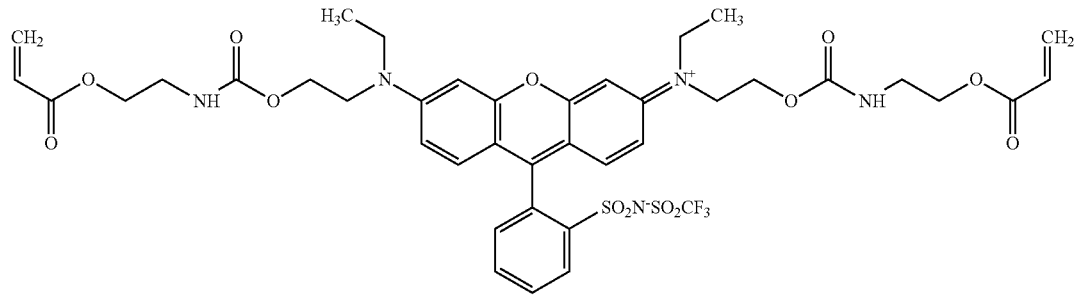

[Chemical Formula 15-1]
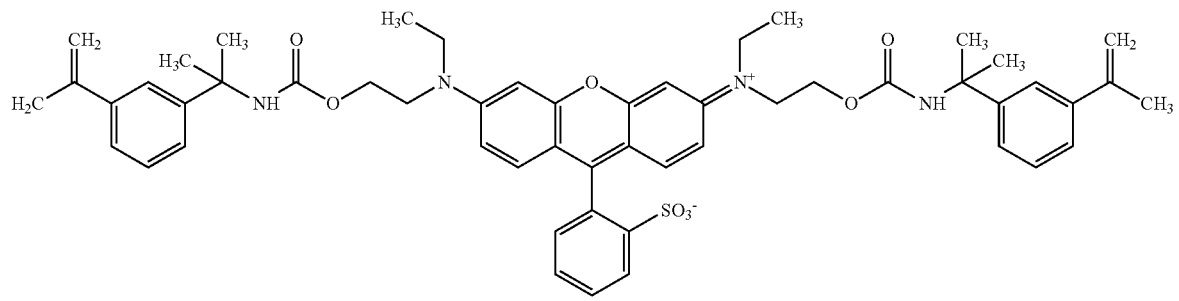
[Chemical Formula 15-2]
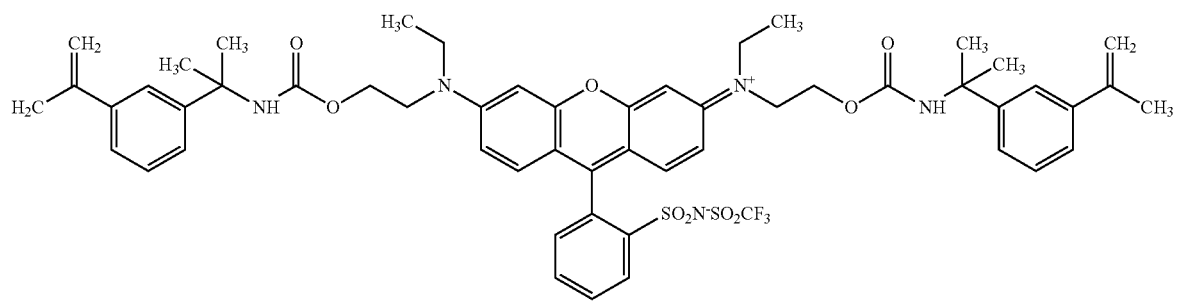
[Chemical Formula 16-1]
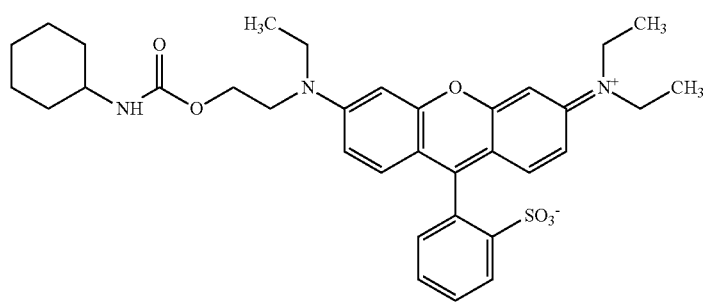
[Chemical Formula 16-2]
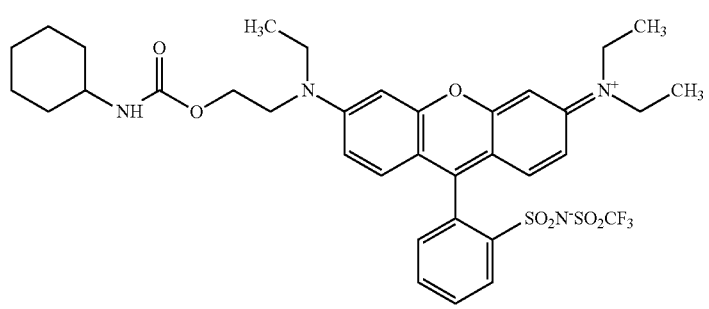
[Chemical Formula 17-1]
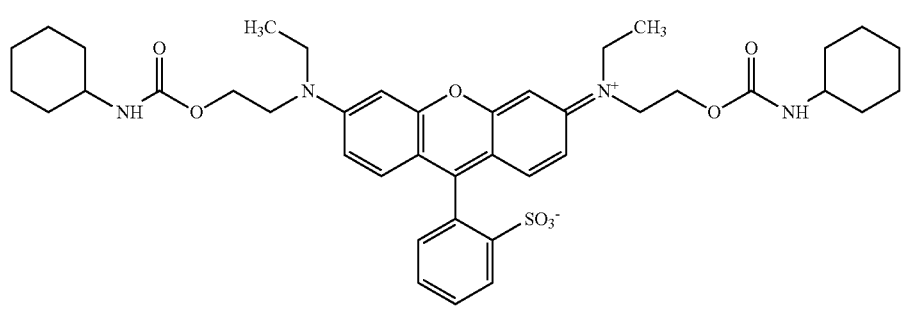

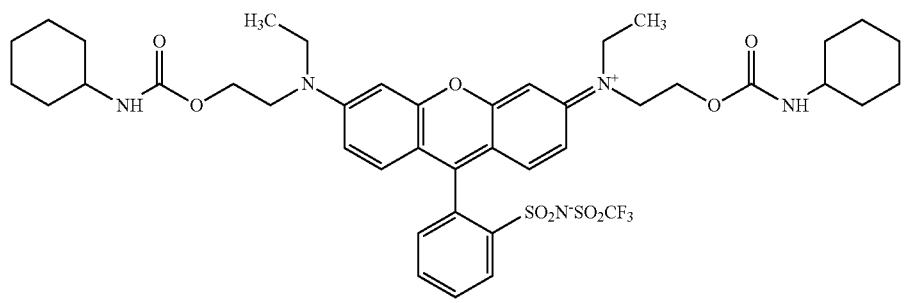

[Chemical Formula 17-2]

The compound represented by Chemical Formula 1 may have maximum absorbance in a wavelength range of about 500 nm to about 600 nm.

The embodiments may be realized by providing an acrylic polymer formed by a copolymerization reaction of a compound represented by Chemical Formula 18 with an ethylenic unsaturated monomer:

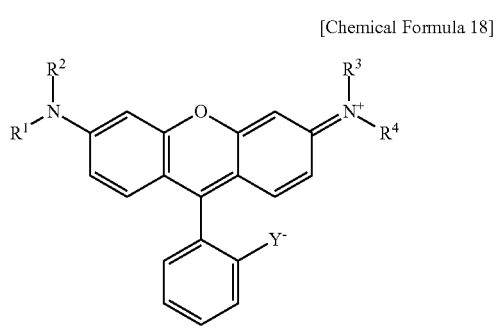

[Chemical Formula 18]

wherein, in Chemical Formula 18, $R^1$ to $R^4$ are each independently a hydrogen, a substituted or unsubstituted C1 to C20 alkyl group, a substituted or unsubstituted C2 to C20 alkenyl group, a substituted or unsubstituted C3 to C20 cycloalkyl group, a substituted or unsubstituted C6 to C20 aryl group, a substituted or unsubstituted C2 to C20 heteroaryl group or a group represented by Chemical Formula 2, at least one of R' to $R^4$ being a group represented by Chemical Formula 2,

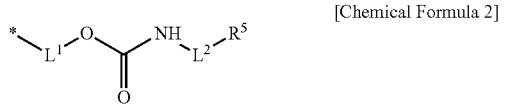

[Chemical Formula 2]

wherein, in Chemical Formula 2, $L^1$ is a substituted or unsubstituted C1 to C20 alkylene group, $L^2$ is a single bond, a substituted or unsubstituted C1 to C20 alkylene group, a substituted or unsubstituted C3 to C20 cycloalkylene group, or a substituted or unsubstituted C6 to C20 arylene group, $R^5$ is a substituent including an ethylenic unsaturated double bond, and Y is *—$SO_3$ or *—$SO_2NSO_2CF_3$, wherein * is a bonding site.

The ethylenic unsaturated monomer may be an aromatic vinyl compound, a unsaturated carboxylate ester compound, an unsaturated amino alkyl carboxylate ester compound, a vinyl carboxylate ester compound, an unsaturated glycidyl carboxylate ester compound, a vinyl cyanide compound, an unsaturated amide compound, or a combination thereof.

The embodiments may be realized by providing a photosensitive resin composition comprising the colorant according to an embodiment.

The photosensitive resin composition may further include a binder resin, a photopolymerizable compound, a photopolymerization initiator, and a solvent.

The binder resin may include an acryl-based binder resin, a cardo-based binder resin, or a combination thereof.

The embodiments may be realized by providing a colorant comprising the compound and/or the acrylic polymer according to an embodiment.

The colorant may be a dye.

The dye may be a red dye or a violet dye.

The embodiments may be realized by providing a color filter manufactured using the photosensitive resin composition according to an embodiment.

DETAILED DESCRIPTION

Example embodiments will now be described more fully hereinafter; however, they may be embodied in different forms and should not be construed as limited to the embodiments set forth herein. Rather, these embodiments are provided so that this disclosure will be thorough and complete, and will fully convey exemplary implementations to those skilled in the art.

It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present.

As used herein, when specific definition is not otherwise provided, the term "substituted" refers to one substituted with a substituent selected from a halogen (F, Br, Cl, or I), a hydroxy group, a nitro group, a cyano group, an amino group ($NH_2$, $NH(R^{200})$ or $N(R^{201})(R^{202})$, wherein $R^{200}$, $R^{201}$, and $R^{202}$ are the same or different, and are independently a C1 to C10 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group, and a substituted or unsubstituted heterocyclic group.

As used herein, when specific definition is not otherwise provided, the term "alkyl group" refers to a C1 to C20 alkyl group, and specifically a C1 to C15 alkyl group, the term "cycloalkyl group" refers to a C3 to C20 cycloalkyl group, and specifically a C3 to C18 cycloalkyl group, the term "alkoxy group" refers to a C1 to C20 alkoxy group, and specifically a C1 to C18 alkoxy group, the term "aryl group" refers to a C6 to C20 aryl group, and specifically a C6 to C18 aryl group, the term "alkenyl group" refers to a C2 to C20 alkenyl group, and specifically a C2 to C18 alkenyl group, the term "alkylene group" refers to a C1 to C20 alkylene group, and specifically C1 to C18 alkylene group, and the term "arylene group" refers to a C6 to C20 arylene group, and specifically a C6 to C16 arylene group.

As used herein, when specific definition is not otherwise provided, "(meth)acrylate" refers to "acrylate" and "methacrylate" and "(meth)acrylic acid" refers to "acrylic acid" and "methacrylic acid."

As used herein, when a definition is not otherwise provided, the term "combination" refers to mixing or copolymerization. In addition, "copolymerization" may refer to, e.g., block copolymerization or random copolymerization, and "copolymer" may refer to, e.g., a block copolymer or a random copolymer.

In the chemical formula of the present specification, unless a specific definition is otherwise provided, hydrogen may be bonded at the position when a chemical bond is not drawn where supposed to be given.

In the present specification, a cardo-based resin refers to a resin including at least one functional group selected from Chemical Formula 20-1 to Chemical Formula 20-11.

As used herein, when a definition is not otherwise provided, the term "ethylenic unsaturated double bond" refers to a "carbon-carbon double bond", and the ethylenic unsaturated monomer refers to a monomer including the ethylenic unsaturated double bond.

As used herein, when a specific definition is not otherwise provided, "*" indicates a point where the same or different atom or chemical formula is linked.

An embodiment provides a compound represented by Chemical Formula 1.

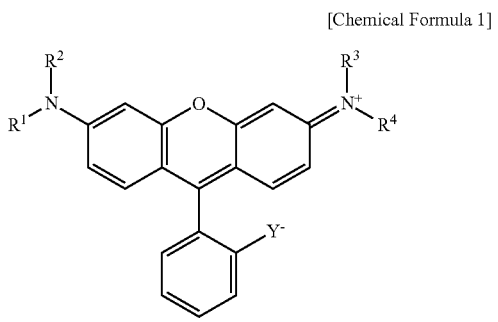

[Chemical Formula 1]

In Chemical Formula 1, $R^1$ to $R^4$ may each independently be or include, e.g., a hydrogen, a substituted or unsubstituted C1 to C20 alkyl group, a substituted or unsubstituted C2 to C20 alkenyl group, a substituted or unsubstituted C3 to C20 cycloalkyl group, a substituted or unsubstituted C6 to C20 aryl group, a substituted or unsubstituted C2 to C20 heteroaryl group or a group represented by Chemical Formula 2. In an implementation, at least one of $R^1$ to $R^4$ is a group represented by Chemical Formula 2.

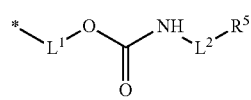

[Chemical Formula 2]

In Chemical Formula 2, $L^1$ may be or may include, e.g., a substituted or unsubstituted C1 to C20 alkylene group, $L^2$ may be or may include, e.g., a single bond, a substituted or unsubstituted C1 to C20 alkylene group, a substituted or unsubstituted C3 to C20 cycloalkylene group or a substituted or unsubstituted C6 to C20 arylene group, $R^5$ may be or may include, e.g., a substituted or unsubstituted C3 to C20 cycloalkyl group or a substituent including an ethylenic unsaturated double bond, and Y may be, e.g., *—$SO_3$ or *—$SO_2NSO_2CF_3$.

As described above, a color filter manufactured by using a pigment-type photosensitive resin composition may have a limit in terms of luminance and a contrast ratio due to a pigment particle size. In addition, a color image sensor device for an image sensor may use a smaller dispersion particle diameter to form a fine pattern. In order to correspond to the requirements, an attempt to realize a color filter having improved luminance and a contrast ratio has been made by introducing a dye forming no particle (instead of the pigment) to prepare a photosensitive resin composition appropriate for the dye.

A photosensitive resin composition including a xanthene-based compound in which a charge is separated may have very low solubility in an organic solvent such as PGMEA, may exhibit deteriorated heat resistance and chemical resistance, and the xanthene-based compound as a colorant may have a limit of being used in the photosensitive resin composition. However, a compound according to an embodiment, e.g., a compound represented by Chemical Formula 1 may include at least one substituent or group represented by Chemical Formula 2 and thus may exhibit improved solubility in an organic solvent. Accordingly, a photosensitive resin composition including the compound may be used to help improve luminance and a contrast ratio of a color filter.

At least two of $R^1$ to $R^4$ may be groups represented by Chemical Formula 2. When the compound according to an embodiment includes at least two substituents represented by Chemical Formula 2, solubility in an organic solvent and luminance provided by a composition including the compound may be further improved. A compound including one functional group represented by Chemical Formula 2 may be synthesized by adjusting contents of reactants (compared with the compound including at least two functional groups represented by Chemical Formula 2) and may be synthesized by referring to a method of synthesizing the compound including at least two functional groups represented by Chemical Formula 2.

In an implementation, R' or $R^2$ may be a group represented by Chemical Formula 2.

In an implementation, $R^1$ or $R^2$ may be a group represented by Chemical Formula 2, and simultaneously $R^3$ or $R^4$ may be a group represented by Chemical Formula 2.

The $R^5$ may be, e.g., a substituted or unsubstituted C3 to C20 cycloalkyl group, a substituted or unsubstituted acrylate group, a substituted or unsubstituted C2 to C20 alkenyl group, or a C6 to C20 aryl group including a substituent having an ethylenic unsaturated double bond at a terminal end thereof.

In an implementation, the substituted or unsubstituted C3 to C20 cycloalkyl group may be an unsubstituted cyclohexyl group, the substituted or unsubstituted acrylate group may be a group represented by Chemical Formula 4, the substituted or unsubstituted C2 to C20 alkenyl group may be a group represented by Chemical Formula 3, and the C6 to C20 aryl group including a substituent having an ethylenic unsaturated double bond at the terminal end may be a group represented by Chemical Formula 5.

[Chemical Formula 3]

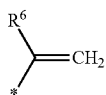

[Chemical Formula 4]

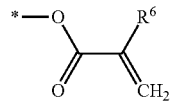

[Chemical Formula 5]

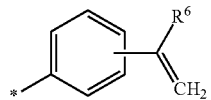

In Chemical Formulae 3 to 5, $R^6$ may be or may include, e.g., a hydrogen atom or a substituted or unsubstituted C1 to C5 alkyl group.

In an implementation, the compound represented by Chemical Formula 1 may be, e.g., a compound represented by one of Chemical Formula 6-1 to Chemical Formula 17-2.

[Chemical Formula 6-1]

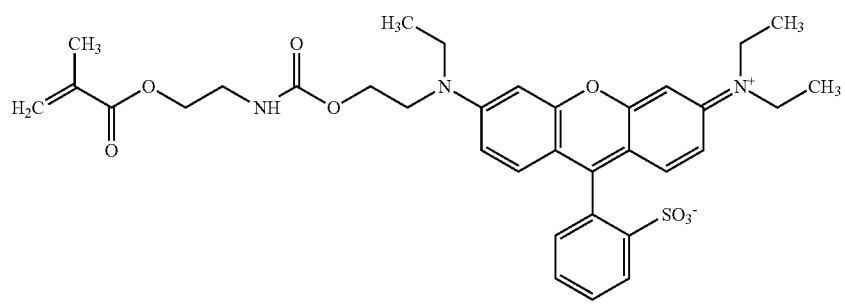

[Chemical Formula 6-2]

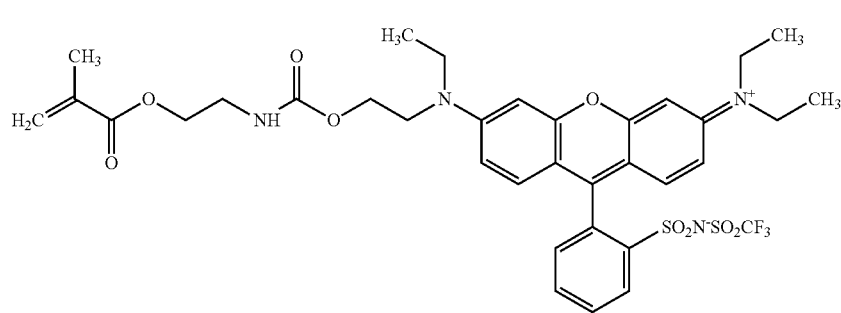

[Chemical Formula 7-1]

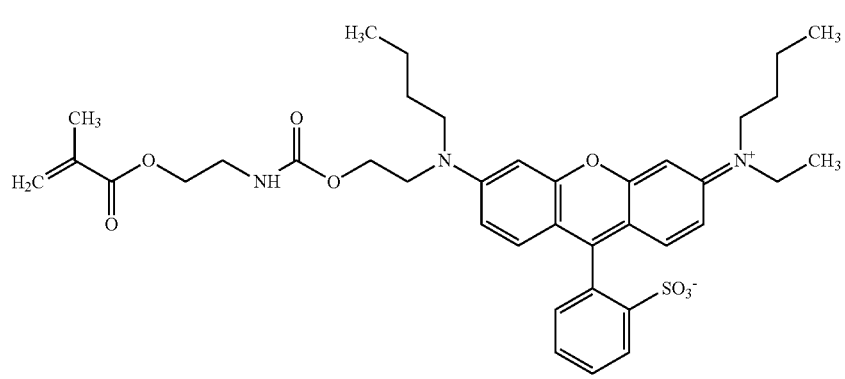

[Chemical Formula 7-2]
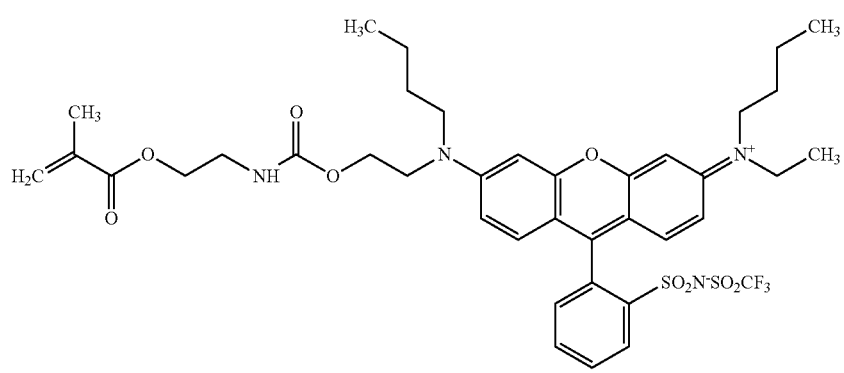
[Chemical Formula 8-1]
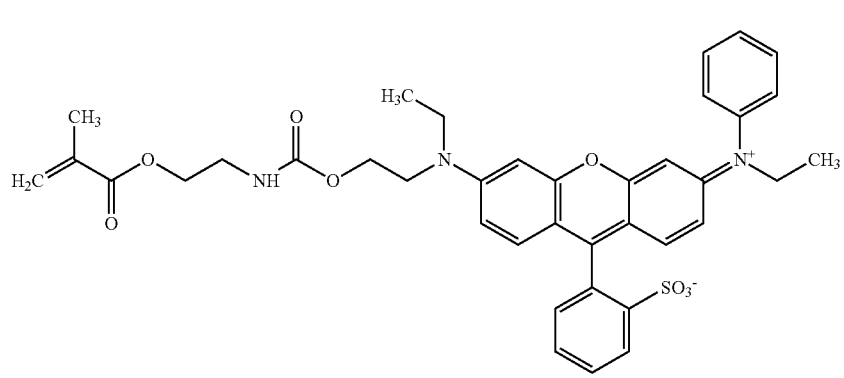
[Chemical Formula 8-2]
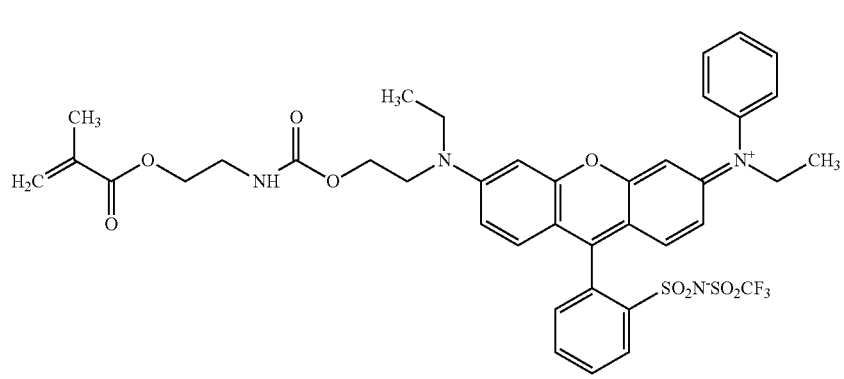
[Chemical Formula 9-1]
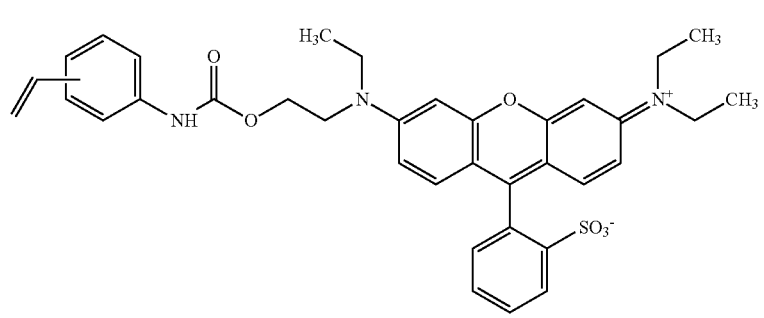

[Chemical Formula 9-2]
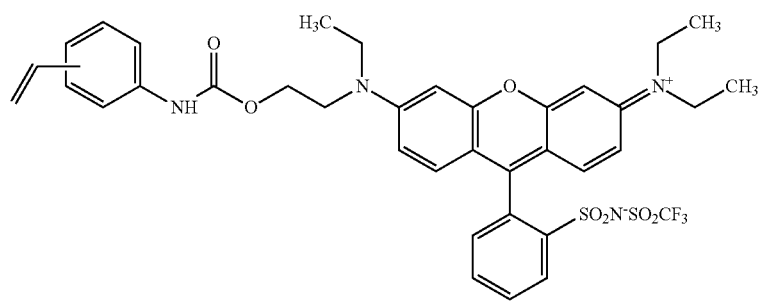
[Chemical Formula 10-1]
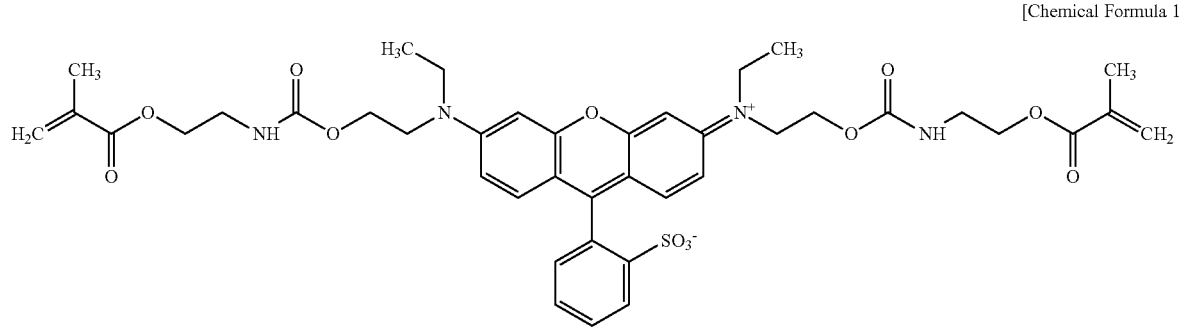
[Chemical Formula 10-2]
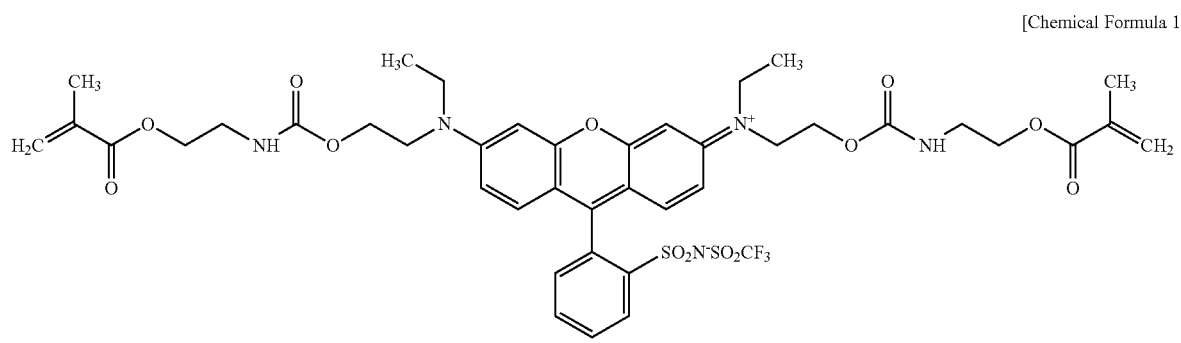
[Chemical Formula 11-1]
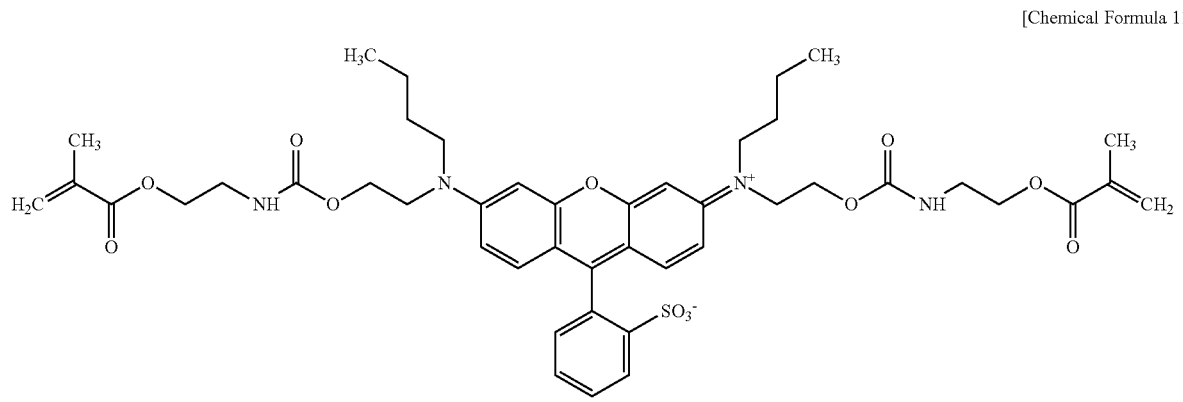

-continued
[Chemical Formula 11-2]
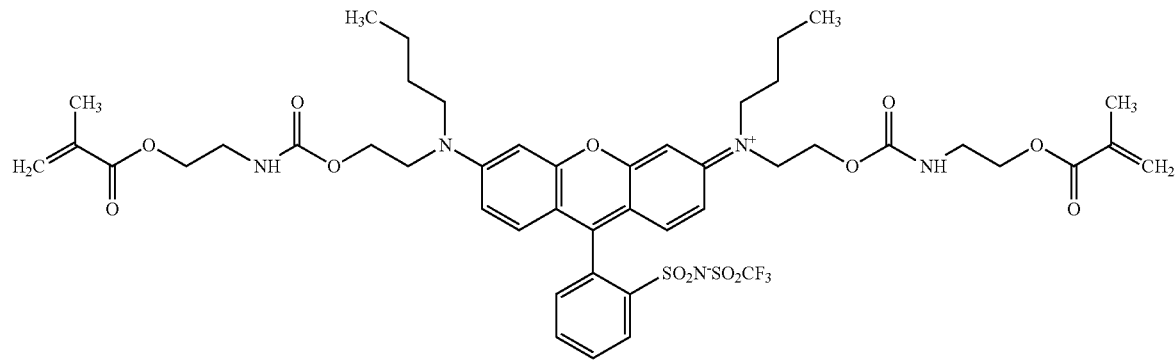
[Chemical Formula 12-1]
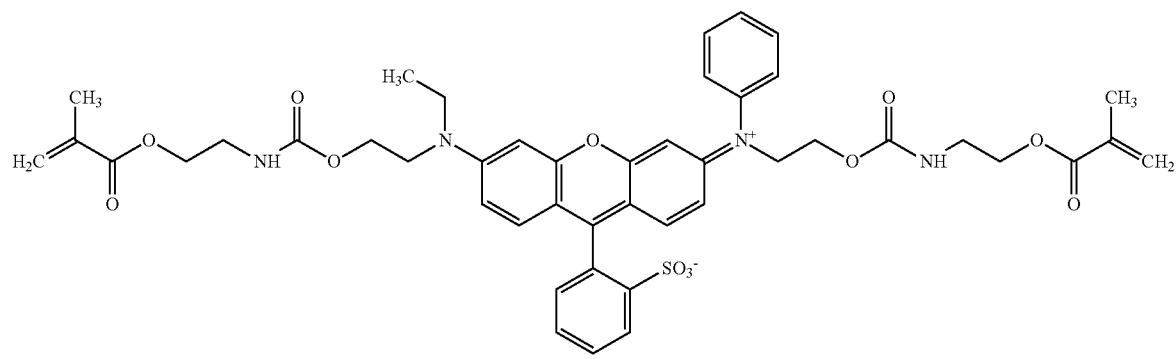
[Chemical Formula 12-2]
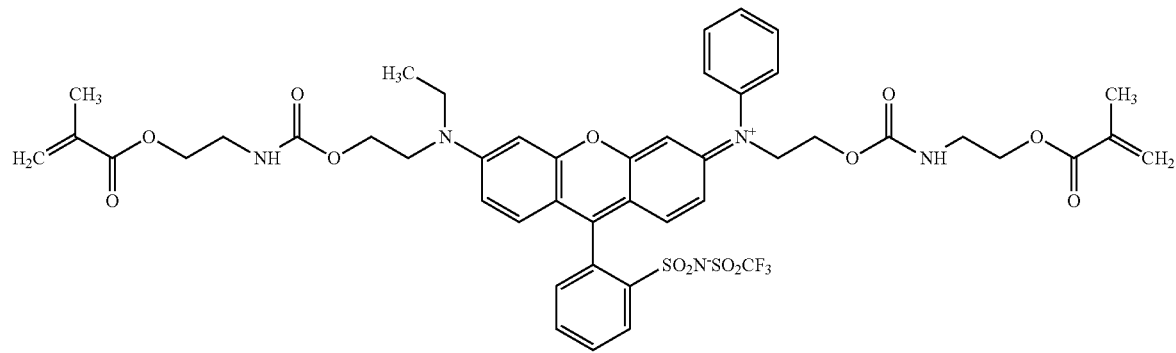
[Chemical Formula 13-1]
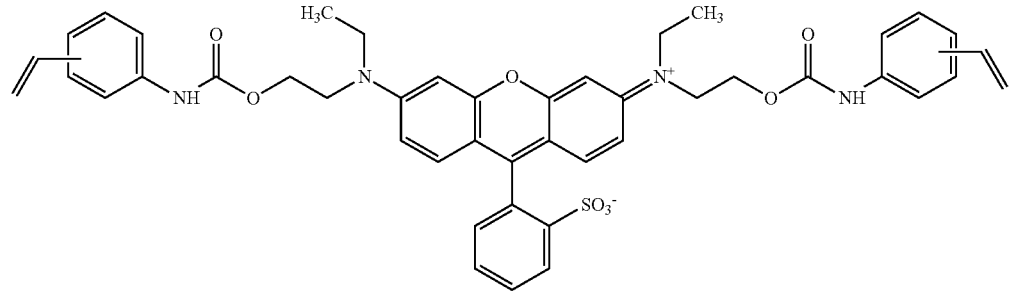

-continued
[Chemical Formula 13-2]
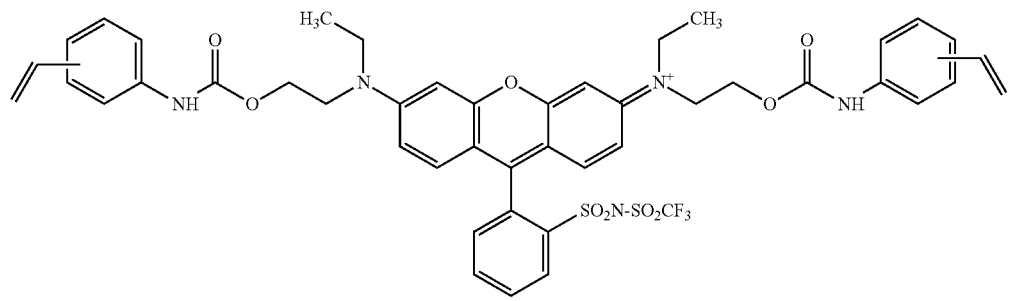
[Chemical Formula 14-1]
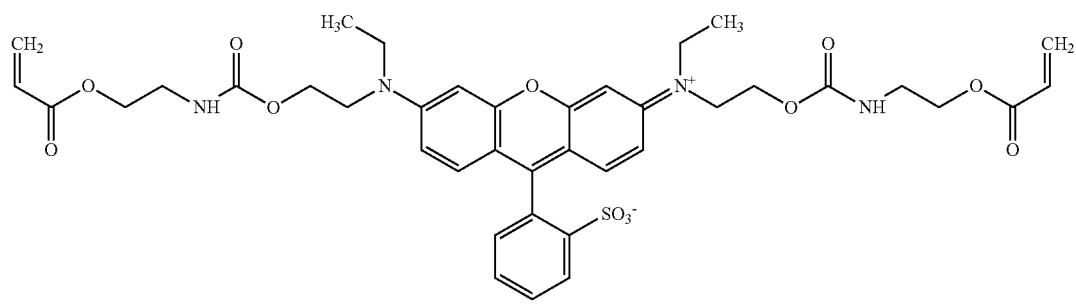
[Chemical Formula 14-2]
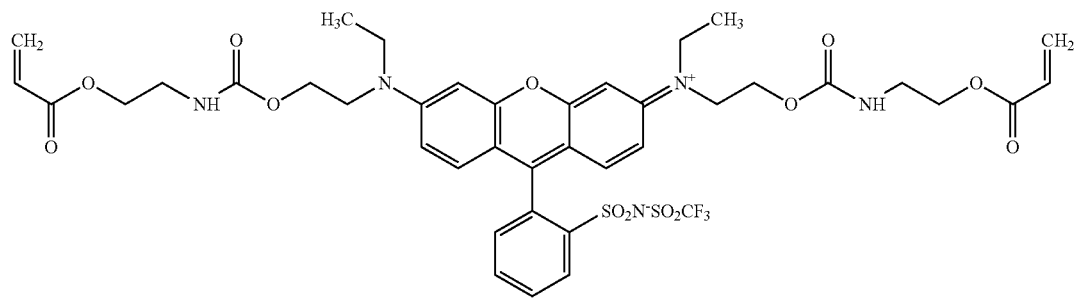
[Chemical Formula 15-1]
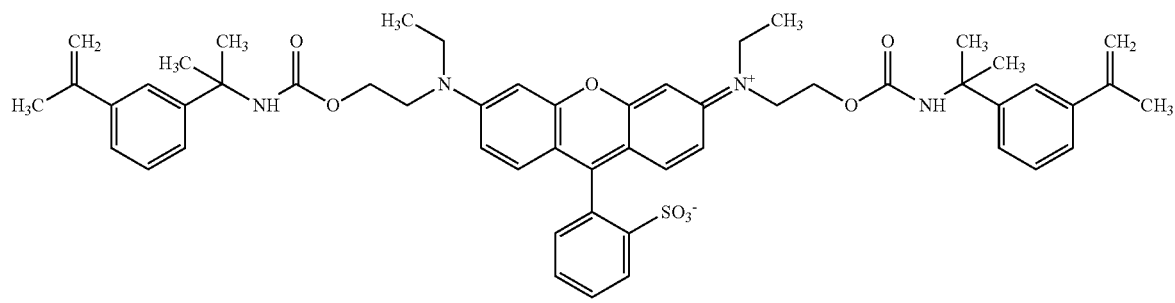
[Chemical Formula 15-2]
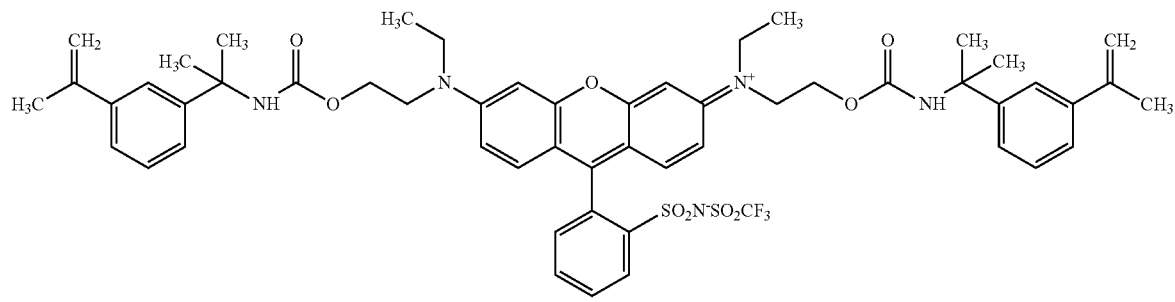

[Chemical Formula 16-1]

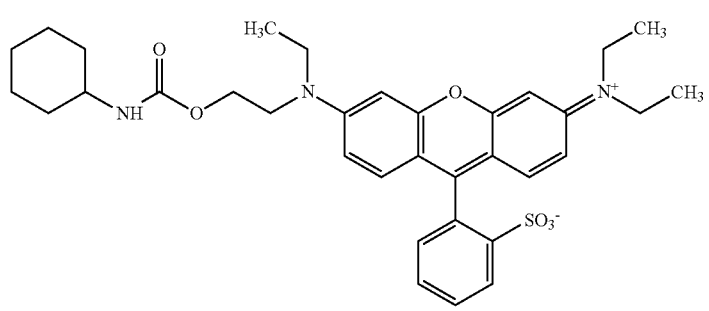

[Chemical Formula 16-2]

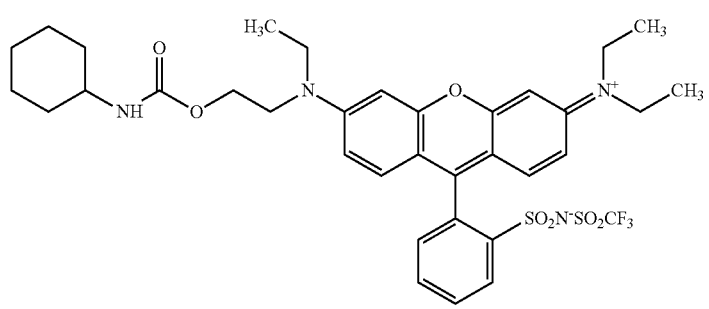

[Chemical Formula 17-1]

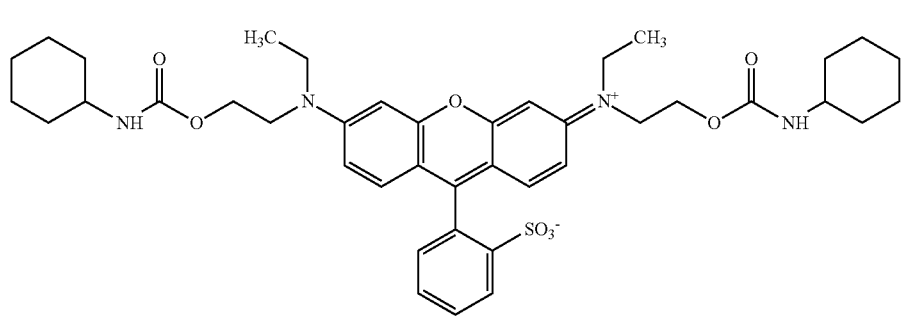

[Chemical Formula 17-2]

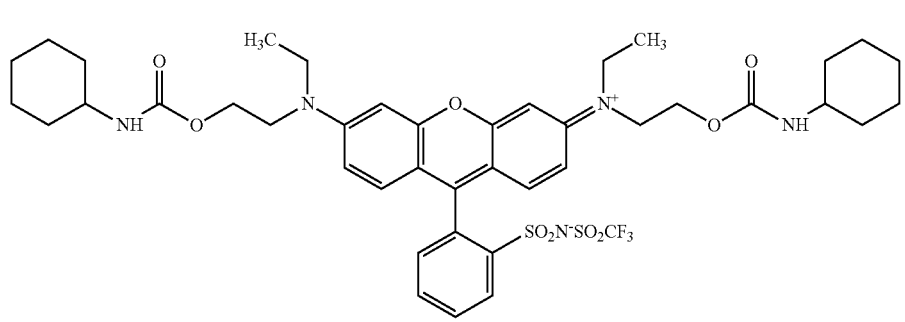

In an implementation, the compound represented by Chemical Formula 1 may have maximum absorbance in a wavelength range of about 500 nm to about 600 nm.

Another embodiment provides a polymer formed by a copolymerization reaction of a compound represented by Chemical Formula 18 with another monomer. The compound represented by Chemical Formula 18 may be the same as the compound represented by Chemical Formula 1, above. In an implementation, the other monomer may be an ethylenic unsaturated monomer. In an implementation, the polymer may be an acrylic polymer.

[Chemical Formula 18]

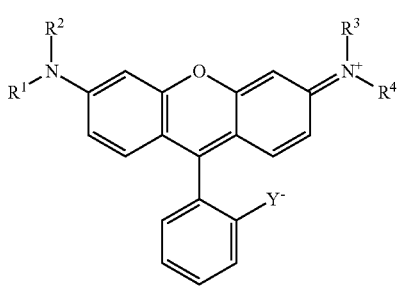

In Chemical Formula 18, $R^1$ to $R^4$ may each independently be or include, e.g., a hydrogen, a substituted or unsubstituted C1 to C20 alkyl group, a substituted or unsubstituted C2 to C20 alkenyl group, a substituted or unsubstituted C3 to C20 cycloalkyl group, a substituted or unsubstituted C6 to C20 aryl group, a substituted or unsubstituted C2 to C20 heteroaryl group or a group represented by Chemical Formula 2.

In an implementation, at least one of $R^1$ to $R^4$ may be a group represented by Chemical Formula 2.

[Chemical Formula 2]

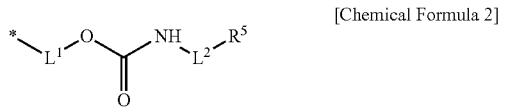

In Chemical Formula 2, $L^1$ may be or may include, e.g., a substituted or unsubstituted C1 to C20 alkylene group, $L^2$ may be or may include, e.g., a single bond, a substituted or unsubstituted C1 to C20 alkylene group, a substituted or unsubstituted C3 to C20 cycloalkylene group, or a substituted or unsubstituted C6 to C20 arylene group, $R^5$ may be or may include, e.g., a substituent including an ethylenic unsaturated double bond, and Y may be, e.g., *—$SO_3$ or *—$SO_2NSO_2CF_3$.

In an implementation, the ethylenic unsaturated monomer may include, e.g., an aromatic vinyl compound, an unsaturated carboxylate ester compound, an unsaturated amino alkyl carboxylate ester compound, a vinyl carboxylate ester compound, an unsaturated glycidyl carboxylate ester compound, a vinyl cyanide compound, a unsaturated amide compound, or a combination thereof.

In an implementation, the ethylenic unsaturated monomer may include, e.g., an aromatic vinyl compound such as styrene, α-methylstyrene, vinyltoluene, vinylbenzylmethylether, and the like; an unsaturated carboxylate ester compound such as (meth)acrylate, methyl(meth)acrylate, ethyl (meth)acrylate, butyl(meth)acrylate, 2-ethylhexyl acrylate, 2-hydroxyethyl(meth)acrylate, 2-hydroxy butyl(meth)acrylate, benzyl(meth)acrylate, cyclohexyl(meth)acrylate, phenyl(meth)acrylate, and the like; an unsaturated amino alkyl carboxylate ester compound such as 2-aminoethyl(meth) acrylate, 2-dimethylaminoethyl(meth)acrylate, and the like; a vinyl carboxylate ester compound such as vinyl acetate, vinyl benzoate and the like; an unsaturated glycidyl carboxylate ester compound such as glycidyl(meth)acrylate, and the like; a vinyl cyanide compound such as (meth) acrylonitrile, and the like; an unsaturated amide compound such as (meth)acrylamide, and the like, or a combination thereof.

An acrylic polymer as a product of a copolymerization of the compound represented by Chemical Formula 18 and the ethylenic unsaturated monomer may have excellent heat resistance and processibility and may be used as a useful colorant in a photosensitive resin composition for a color filter.

In an implementation, an acrylic polymer obtained through a copolymerization reaction of a compound represented by Chemical Formula 10-1 and methylmethacrylate may be a copolymer represented by Chemical Formula 19.

[Chemical Formula 19]

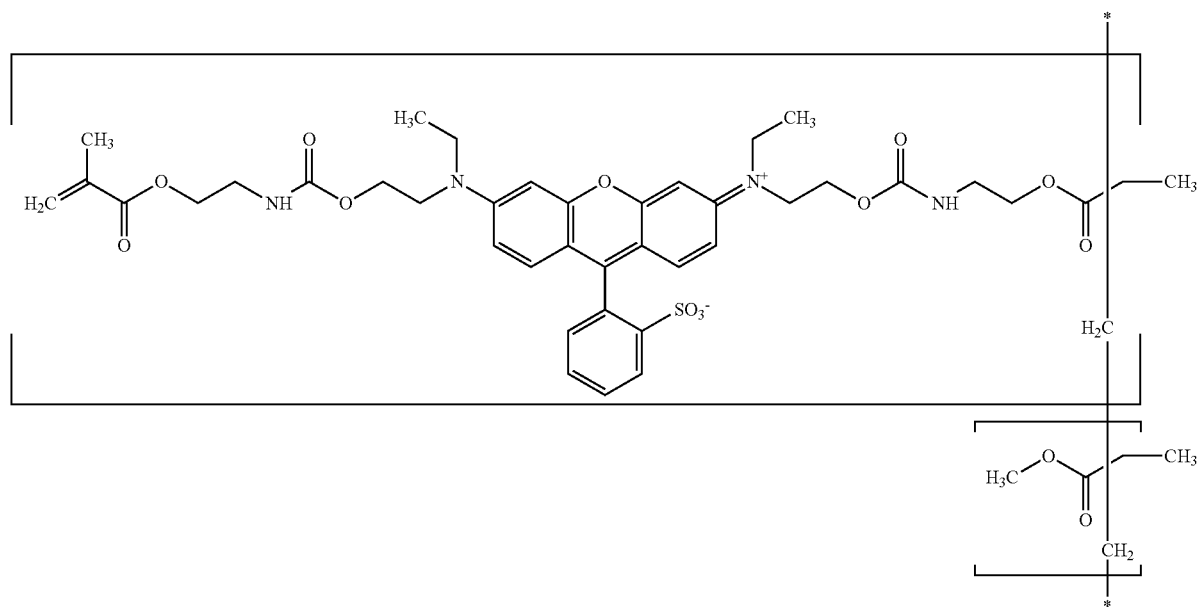

Another embodiment provides a colorant including the compound and/or the acrylic polymer.

In an implementation, the colorant may be a dye, e.g., a red dye or a violet dye.

Another embodiment provides a photosensitive resin composition including the colorant.

The photosensitive resin composition may further include, e.g., a binder resin, a photopolymerizable compound, a photopolymerization initiator, and a solvent.

Hereinafter each component is specifically described.

Colorant

In an implementation, the colorant may further include an organic solvent-soluble dye in addition to the compound and/or the acrylic polymer.

Examples of the organic solvent-soluble dye may include a triarylmethane-based compound, an anthraquinone-based compound, a benzylidene-based compound, a cyanine-based compound, a phthalocyanine-based compound, an azaporphyrin-based compound, an indigo-based compound, and the like.

In an implementation, the colorant may further include a pigment in addition to the compound and/or the acrylic polymer.

The pigment may include, e.g., a blue pigment, a violet pigment, a red pigment, a green pigment, a yellow pigment, and the like.

Examples of the blue pigment may include C.I. blue pigment 15:6, C.I. blue pigment 15, C.I. blue pigment 15:1, C.I. blue pigment 15:2, C.I. blue pigment 15:3, C.I. blue pigment 15:4, C.I. blue pigment 15:5, C.I. blue pigment 16, C.I. blue pigment 22, C.I. blue pigment 60, C.I. blue pigment 64, C.I. blue pigment 80, or a combination thereof.

Examples of the violet pigment may include C.I violet pigment 1, C.I violet pigment 19, C.I violet pigment 23, C.I violet pigment 27, C.I violet pigment 29, C.I violet pigment 30, C.I violet pigment 32, C.I violet pigment 37, C.I violet pigment 40, C.I violet pigment 42, C.I violet pigment 50, or a combination thereof.

Examples of the red pigment may include a perylene-based pigment, an anthraquinone-based pigment, a dianthraquinone-based pigment, an azo-based pigment, a diazo-based pigment, a quinacridone-based pigment, an anthracene-based pigment, and the like. Specific examples of the red pigment may be a perylene pigment, a quinacridone pigment, naphthol AS, a sicomin pigment, an anthraquinone (sudan I, II, III, R), dianthraquinonylate, bis azo, benzopyrane, and the like.

Examples of the green pigment may include a halogenated phthalocyanine-based pigment such as C.I. pigment green 58 or C.I. pigment green 59.

Examples of the yellow pigment may include a C.I. pigment yellow 139, a C.I. pigment yellow 138, a C.I. pigment yellow 150, and the like, and may be used singularly or as a mixture of two or more.

The pigment may be included in a form of pigment dispersion liquid in the photosensitive resin composition.

The pigment dispersion liquid may include a solid pigment, a solvent, and a dispersing agent in order to disperse the pigment in the solvent uniformly.

In an implementation, the pigment may be included in a solid content of about 1 wt % to about 20 wt %, for example about 8 wt % to about 20 wt %, for example about 8 wt % to about 15 wt %, for example about 10 wt % to about 20 wt %, for example about 10 wt % to about 15 wt % based on the total amount of pigment dispersion liquid.

The dispersing agent may be, e.g., a non-ionic dispersing agent, an anionic dispersing agent, a cationic dispersing agent, and the like. Examples of the dispersing agent may include polyalkylene glycol and esters thereof, polyoxyalkylene, polyhydric alcohol ester alkylene oxide addition product, alcoholalkylene oxide addition product, sulfonate ester, sulfonate salt, a carboxylate ester, a carboxylate salt, an alkylamide alkylene oxide addition product, alkyl amine, and the like, and may be used singularly or as a mixture of two or more.

Commercially available examples of the dispersing agent may include DISPERBYK-101, DISPERBYK-130, DISPERBYK-140, DISPERBYK-160, DISPERBYK-161, DISPERBYK-162, DISPERBYK-163, DISPERBYK-164, DISPERBYK-165, DISPERBYK-166, DISPERBYK-170, DISPERBYK-171, DISPERBYK-182, DISPERBYK-2000, DISPERBYK-2001, and the like made by BYK Co., Ltd.; EFKA-47, EFKA-47EA, EFKA-48, EFKA-49, EFKA-100, EFKA-400, EFKA-450, and the like made by EFKA Chemicals Co.; Solsperse 5000, Solsperse 12000, Solsperse 13240, Solsperse 13940, Solsperse 17000, Solsperse 20000, Solsperse 24000GR, Solsperse 27000, Solsperse 28000, and the like made by Zeneka Co.; or PB711, or PB821 made by Ajinomoto Inc.

The dispersing agent may be included in an amount of about 1 to about 20 wt % based on the total weight of the pigment dispersion liquid. When the dispersing agent is included within the range, dispersion of a photosensitive resin composition is improved due to an appropriate viscosity, and thus optical, physical, and chemical quality may be maintained when the photosensitive resin composition is applied to products.

The solvent for forming the pigment dispersion liquid may include ethylene glycol acetate, ethylcellosolve, propylene glycol monomethyl ether acetate, ethyllactate, polyethylene glycol, cyclohexanone, propylene glycol methylether, and the like.

Binder Resin

In an implementation, the binder resin may be an acryl-based binder resin, a cardo-based binder resin, or a combination thereof. For example, the binder resin may be an acryl-based binder resin.

The acryl-based binder resin may include, e.g., a copolymer of a first ethylenic unsaturated monomer and a second ethylenic unsaturated monomer that is copolymerizable therewith, and is resin including at least one acryl-based repeating unit.

The first ethylenic unsaturated monomer may include, e.g., an ethylenic unsaturated monomer including at least one carboxyl group. Examples of the monomer may include (meth)acrylic acid, maleic acid, itaconic acid, fumaric acid, or a combination thereof.

The first ethylenic unsaturated monomer may be included in an amount of about 5 to about 50 wt %, e.g., about 10 to about 40 wt %, based on the total amount of the acryl-based binder resin.

The second ethylenic unsaturated monomer may include, e.g., an aromatic vinyl compound such as styrene, α-methylstyrene, vinyl toluene, vinylbenzylmethylether and the like; an unsaturated carboxylate ester compound such as methyl(meth)acrylate, ethyl(meth)acrylate, butyl(meth)acrylate, 2-hydroxyethyl(meth)acrylate, 2-hydroxy butyl (meth)acrylate, benzyl(meth)acrylate, cyclohexyl(meth)acrylate, phenyl(meth)acrylate, and the like; an unsaturated amino alkyl carboxylate ester compound such as 2-aminoethyl(meth)acrylate, 2-dimethylaminoethyl(meth)acrylate, and the like; a carboxylic acid vinyl ester compound such as vinyl acetate, vinyl benzoate, and the like; an unsaturated glycidyl carboxylate ester compound such as glycidyl(meth)acrylate, and the like; a vinyl cyanide compound such as (meth)acrylonitrile and the like; an unsaturated amide compound such as (meth)acrylamide, and the like; and the like, and may be used singularly or as a mixture of two or more.

Examples of the acryl-based binder resin may include a polybenzylmethacrylate copolymer, an acrylic acid/benzylmethacrylate copolymer, a methacrylic acid/benzylmethacrylate copolymer, a methacrylic acid/benzylmethacrylate/styrene copolymer, a methacrylic acid/benzylmethacrylate/2-hydroxyethylmethacrylate copolymer, a methacrylic acid/benzylmethacrylate/styrene/2-hydroxyethylmethacrylate copolymer, and the like, but are not limited thereto. These may be used singularly or as a mixture of two or more.

In an implementation, the acryl-based binder resin may have a weight average molecular weight of about 3,000 g/mol to about 150,000 g/mol, e.g., about 5,000 g/mol to about 50,000 g/mol, or about 20,000 g/mol to about 30,000 g/mol. When the acryl-based binder resin has a weight average molecular weight within the range, the photosensitive resin composition has good physical and chemical properties, appropriate viscosity, and close contacting properties with a substrate during manufacture of a color filter.

In an implementation, the acryl-based binder resin may have an acid value of about 15 mgKOH/g to about 60 mgKOH/g, for example about 20 mgKOH/g to about 50 mgKOH/g. When the acryl-based binder resin has an acid value within the range, a pixel pattern may have excellent resolution.

In an implementation, the cardo-based binder resin may include a repeating unit represented by Chemical Formula 20.

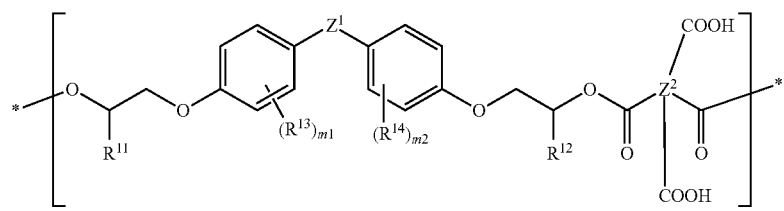

[Chemical Formula 20]

In Chemical Formula 20, $R^{11}$ and $R^{12}$ may each independently be or include, e.g., a hydrogen atom or a substituted or unsubstituted (meth)acryloyloxyalkyl group, $R^{13}$ and $R^{14}$ may each independently be or include, e.g., a hydrogen atom, a halogen atom or a substituted or unsubstituted C1 to C20 alkyl group, and $Z^1$ may be or may include, e.g., a single bond, O, CO, $SO_2$, $CR^{15}R^{16}$, $SiR^{17}R^{18}$ (wherein, $R^{15}$ to $R^{18}$ are independently a hydrogen atom or a substituted or unsubstituted C1 to C20 alkyl group) or a linking group represented by one of Chemical Formula 20-1 to Chemical Formula 20-11,

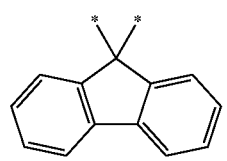

[Chemical Formua 20-1]

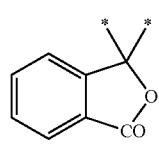

[Chemical Formula 20-2]

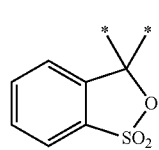

[Chemical Formula 20-3]

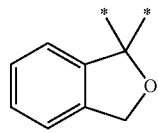

[Chemical Formula 20-4]

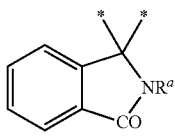

[Chemical Formula 20-5]

In Chemical Formula 20-5, $R^a$ may be, e.g., a hydrogen atom, an ethyl group, $C_2H_4Cl$, $C_2H_4OH$, $CH_2CH=CH_2$, or a phenyl group.

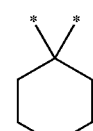

[Chemical Formula 20-6]

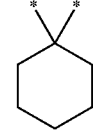

[Chemical Formula 20-7]

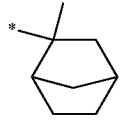

[Chemical Formula 20-8]

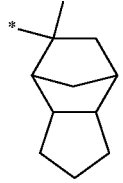

[Chemical Formula 20-9]

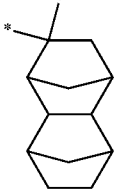

[Chemical Formula 20-10]

[Chemical Formula 20-11]

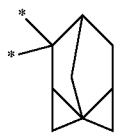

$Z^2$ may be, e.g., an acid dianhydride residual group, and m1 and m2 may each independently be, e.g., an integer ranging from 0 to 4.

The cardo-based binder resin may include a functional group represented by Chemical Formula 21 at a terminal end.

[Chemical Formula 21]

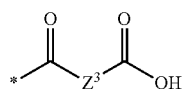

In Chemical Formula 21, $Z^3$ may be, e.g., a group represented by Chemical Formulae 21-1 to 21-7.

[Chemical Formula 21-1]

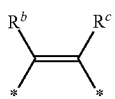

In Chemical Formula 21-1, $R^b$ and $R^c$ may each independently be or include, e.g., a hydrogen atom, a substituted or unsubstituted C1 to C20 alkyl group, an ester group, or an ether group.

[Chemical Formula 21-2]

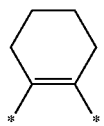

[Chemical Formula 21-3]

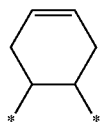

[Chemical Formula 21-4]

[Chemical Formula 21-5]

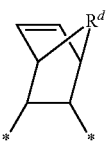

In Chemical Formula 21-5, $R^d$ may be or may include, e.g., O, S, NH, a substituted or unsubstituted C1 to C20 alkylene group, a C1 to C20 alkylamine group, or a C2 to C20 alkenylamine group.

[Chemical Formula 21-6]

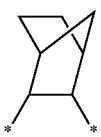

[Chemical Formula 21-7]

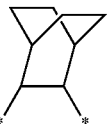

The cardo-based binder resin may be, e.g., prepared by mixing at least two of, a fluorene-containing compound such as 9,9-bis (4-oxiranylmethoxyphenyl)fluorene; an anhydride compound such as benzenetetracarboxylic acid dianhydride, naphthalenetetracarboxylic acid dianhydride, biphenyltetracarboxylic acid dianhydride, benzophenonetetracarboxylic acid dianhydride, pyromellitic dianhydride, cyclobutanetetracarboxylic acid dianhydride, perylenetetracarboxylic acid dianhydride, tetrahydrofurantetracarboxylic acid dianhydride, and tetrahydrophthalic anhydride; a glycol compound such as ethylene glycol, propylene glycol, and polyethylene glycol; an alcohol compound such as methanol, ethanol, propanol, n-butanol, cyclohexanol, and benzylalcohol; a solvent-based compound such as propylene glycol methylethylacetate, and N-methylpyrrolidone; a phosphorus compound such as triphenylphosphine; and an amine or ammonium salt compound such as tetramethylammonium chloride, tetraethylammonium bromide, benzyldiethyl amine, triethylamine, tributylamine, benzyltriethylammonium chloride.

When the cardo-based binder resin is used with the acryl-based binder resin, a photosensitive resin composition having an excellent close-contacting force, a high resolution, and high luminescence characteristics may be obtained.

The cardo-based binder resin may have a weight average molecular weight of about 500 g/mol to about 50,000 g/mol, e.g., about 3,000 g/mol to about 30,000 g/mol. When the cardo-based binder resin has a weight average molecular weight within the ranges, a satisfactory pattern may be formed without a residue during a manufacture of a color filter and without losing a film thickness during development.

The cardo-based binder resin may have an acid value of, e.g., about 100 mgKOH/g to about 140 mgKOH/g.

Photopolymerizable Compound

The photopolymerizable compound may be a monofunctional or multi-functional ester of (meth)acrylic acid including at least one ethylenic unsaturated double bond.

The photopolymerizable compound may cause or facilitate sufficient polymerization during exposure in a pattern-forming process and form a pattern having excellent heat resistance, light resistance, and chemical resistance due to the ethylenic unsaturated double bond.

Examples of the photopolymerizable compound may include ethylene glycol di(meth)acrylate, diethylene glycol di(meth)acrylate, triethylene glycol di(meth)acrylate, propylene glycol di(meth)acrylate, neopentyl glycol di(meth)acrylate, 1,4-butanediol di(meth)acrylate, 1,6-hexanediol di(meth)acrylate, bisphenol A di(meth)acrylate, pentaerythritol di(meth)acrylate, pentaerythritol tri(meth)acrylate, pentaerythritol tetra(meth)acrylate, pentaerythritol hexa(meth)acrylate, dipentaerythritol di(meth)acrylate, dipentaerythritol tri(meth)acrylate, dipentaerythritol penta(meth)acrylate, dipentaerythritol hexa(meth)acrylate, bisphenol A epoxy(meth)acrylate, ethylene glycol monomethylether (meth)acrylate, trimethylol propane tri(meth)acrylate, tris(meth)acryloyloxyethyl phosphate, novolacepoxy (meth) acrylate, and the like.

Commercially available examples of the photopolymerizable compound may be as follows. The mono-functional (meth)acrylic acid ester may include Aronix M-101®, M-111®, M-114® (Toagosei Chemistry Industry Co., Ltd.); KAYARAD TC-110S®, TC-120S® (Nippon Kayaku Co., Ltd.); V-158®, V-2311® (Osaka Organic Chemical Ind., Ltd.), and the like. Examples of a difunctional (meth)acrylic acid ester may include Aronix M-210®, M-240®, M-6200® (Toagosei Chemistry Industry Co., Ltd.), KAYARAD HDDA®, HX-220®, R-604® (Nippon Kayaku Co., Ltd.), V-260®, V-312®, V-335 HP® (Osaka Organic Chemical Ind., Ltd.), and the like. Examples of a tri-functional (meth) acrylic acid ester may include Aronix M-309®, M-400®, M-405®, M-450®, M-7100®, M-8030®, M-8060® (Toagosei Chemistry Industry Co., Ltd.), KAYARAD TMPTA®, DPCA-20®, DPCA-30®, DPCA-60®, DPCA-120® (Nippon Kayaku Co., Ltd.), V-295®, V-300®, V-360®, V-GPT®, V-3PA®, V-400® (Osaka Yuki Kayaku Kogyo Co. Ltd.), and the like. These may be used singularly or as a mixture of two or more.

The photopolymerizable compound may be treated with acid anhydride to help improve developability.

Photopolymerizable Initiator

The photopolymerization initiator may be a suitable photopolymerization initiator in a photosensitive resin composition, e.g., an acetophenone-based compound, a benzophenone-based compound, a thioxanthone-based compound, a benzoin-based compound, an oxime-based compound, and the like.

Examples of the acetophenone-based compound may include 2,2'-diethoxy acetophenone, 2,2'-dibutoxy acetophenone, 2-hydroxy-2-methylpropinophenone, p-t-butyltrichloro acetophenone, p-t-butyldichloro acetophenone, 4-chloro acetophenone, 2,2'-dichloro-4-phenoxy acetophenone, 2-methyl-1-(4-(methylthio)phenyl)-2-morpholinopropan-1-one, 2-benzyl-2-dimethylamino-1-(4-morpholinophenyl)-butan-1-one, and the like.

Examples of the benzophenone-based compound may include benzophenone, benzoyl benzoate, methyl benzoyl benzoate, 4-phenyl benzophenone, hydroxy benzophenone, acrylated benzophenone, 4,4'-bis(dimethyl amino)benzophenone, 4,4'-bis(diethylamino)benzophenone, 4,4'-dimethylaminobenzophenone, 4,4'-dichlorobenzophenone, 3,3'-dimethyl-2-methoxybenzophenone, and the like.

Examples of the thioxanthone-based compound may be thioxanthone, 2-methylthioxanthone, isopropyl thioxanthone, 2,4-diethyl thioxanthone, 2,4-diisopropyl thioxanthone, 2-chlorothioxanthone, and the like.

Examples of the benzoin-based compound may include benzoin, benzoin methyl ether, benzoin ethyl ether, benzoin isopropyl ether, benzoin isobutyl ether, benzyldimethylketal, and the like.

Examples of the triazine-based compound may include 2,4,6-trichloro-s-triazine, 2-phenyl 4,6-bis(trichloromethyl)-s-triazine, 2-(3',4'-dimethoxystyryl)-4,6-bis(trichloromethyl)-s-triazine, 2-(4'-methoxynaphthyl)-4,6-bis(trichloromethyl)-s-triazine, 2-(p-methoxyphenyl)-4,6-bis(trichloromethyl)-s-triazine, 2-(p-tolyl)-4,6-bis(trichloro methyl)-s-triazine, 2-biphenyl 4,6-bis(trichloro methyl)-s-triazine, bis(trichloromethyl)-6-styryl-s-triazine, 2-(naphthol-yl)-4,6-bis(trichloromethyl)-s-triazine, 2-(4-methoxynaphthol-yl)-4,6-bis(trichloromethyp-s-triazine, 2-4-bis(trichloromethyl)-6-piperonyl-s-triazine, 2-4-bis (trichloromethyl)-6-(4-methoxystyryl)-s-triazine, and the like.

Examples of the oxime-based compound may include O-acyloxime-based compound, 2-(O-benzoyloxime)-1-[4-(phenylthio)phenyl]-1,2-octandione, 1-(0-acetyloxime)-1-[9-ethyl-6-(2-methylbenzoyl)-9H-carbazol-3-yl]ethanone. O-ethoxycarbonyl-α-oxyamino-1-phenylpropan-1-one, and the like. Specific examples of the O-acyloxime-based compound may be 1,2-octandione, 2-dimethylamino-2-(4-methylbenzyl)-1-(4-morpholin-4-yl-phenyl)-butan-1-one, 1-(4-phenylsulfanyl phenyl)-butane-1,2-dione 2-oxime-O-benzoate, 1-(4-phenylsulfanyl phenyl)-octane-1,2-dione 2-oxime-O-benzoate, 1-(4-phenylsulfanyl phenyl)-octan-1-one oxime-O-acetate, 1-(4-phenylsulfanyl phenyl)-butan-1-one oxime-O-acetate, and the like.

In an implementation, the photopolymerization initiator may further include a carbazole-based compound, a diketone-based compound, a sulfonium borate-based compound, a diazo-based compound, an imidazole-based compound, a biimidazole-based compound, and the like besides the compound.

The photopolymerization initiator may be used with a photosensitizer capable of causing a chemical reaction by absorbing light and becoming excited and then, transferring its energy.

Examples of the photosensitizer may include tetraethylene glycol bis-3-mercapto propionate, pentaerythritol tetrakis-3-mercapto propionate, dipentaerythritol tetrakis-3-mercapto propionate, and the like.

Solvent

The solvent is a material having compatibility with the compound or the acrylic polymer according to an embodiment, the pigment, the binder resin, the photopolymerizable compound, and the photopolymerization initiator, but not reacting therewith.

Examples of the solvent may include alcohols such as methanol, ethanol, and the like; ethers such as dichloroethyl ether, n-butyl ether, diisoamyl ether, methylphenyl ether, tetrahydrofuran, and the like; glycol ethers such as ethylene glycol monomethylether, ethylene glycol monoethylether, and the like; cellosolve acetates such as methyl cellosolve acetate, ethyl cellosolve acetate, diethyl cellosolve acetate, and the like; carbitols such as methylethyl carbitol, diethyl carbitol, diethylene glycol monomethylether, diethylene glycol monoethylether, diethylene glycol dimethylether, diethylene glycol methylethylether, diethylene glycol diethylether, and the like; propylene glycol alkylether acetates such as propylene glycol methylether acetate, propylene glycol propylether acetate, and the like; aromatic hydrocarbons such as toluene, xylene and the like; ketones such as methylethylketone, cyclohexanone, 4-hydroxy-4-methyl-2-pentanone, methyl-n-propylketone, methyl-n-butylketone, methyl-n-amylketone, 2-heptanone, and the like; saturated aliphatic monocarboxylic acid alkyl esters such as ethyl acetate, n-butyl acetate, isobutyl acetate, and the like; lactate esters such as methyl lactate, ethyl lactate, and the like; oxy acetic acid alkyl esters such as oxy methyl acetate, oxy ethyl acetate, butyl oxyacetate, and the like; alkoxy acetic acid alkyl esters such as methoxy methyl acetate, methoxy ethyl acetate, methoxy butyl acetate, ethoxy methyl acetate, ethoxy ethyl acetate, and the like; 3-oxy propionic acid alkyl esters such as 3-oxy methyl propionate, 3-oxy ethyl propionate, and the like; 3-alkoxy propionic acid alkyl esters such as 3-methoxy methyl propionate, 3-methoxy ethyl propionate, 3-ethoxy ethyl propionate, 3-ethoxy methyl propionate, and the like; 2-oxy propionic acid alkyl esters such as 2-oxy methyl propionate, 2-oxy ethyl propionate, 2-oxy propyl propionate, and the like; 2-alkoxy propionic acid alkyl esters such as 2-methoxy methyl propionate, 2-methoxy ethyl propionate, 2-ethoxy ethyl propionate, 2-ethoxy methyl propionate, and the like; 2-oxy-2-methyl propionic acid esters such 2-oxy-2-methyl methyl propionate, 2-oxy-2-methyl ethyl propionate, and the like, monooxy monocarboxylic acid alkyl esters of 2-alkoxy-2-methyl alkyl propionates such as 2-methoxy-2-methyl methyl propionate, 2-ethoxy-2-methyl ethyl propionate, and the like; esters such as 2-hydroxy ethyl propionate, 2-hydroxy-2-methyl ethyl propionate, hydroxy ethyl acetate, 2-hydroxy-3-methyl methyl butanoate, and the like; ketonate esters such as ethyl pyruvate, and the like. In an implementation, high boiling point solvent such as N-methylformamide, N,N-dimethylformamide, N-methylformanilide, N-methylacetamide, N,N-dimethylacetamide, N-methylpyrrolidone, dimethylsulfoxide, benzylethylether, dihexylether, acetylacetone, isophorone, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate, phenyl cellosolve acetate, and the like may be also used.

In an implementation, considering miscibility and reactivity, glycol ethers such as ethylene glycol monoethylether, and the like; ethylene glycol alkylether acetates such as ethyl cellosolve acetate, and the like; esters such as 2-hydroxy ethyl propionate, and the like; carbitols such as diethylene glycol monomethylether, and the like; propylene glycol alkylether acetates such as propylene glycol methylether acetate, propylene glycol propylether acetate and the like may be used.

The photosensitive resin composition may further include an epoxy compound in order to help improve close-contacting properties with a substrate.

Examples of the epoxy compound may include a phenol novolac epoxy compound, a tetramethyl biphenyl epoxy compound, a bisphenol A epoxy compound, an alicyclic epoxy compound, or a combination thereof.

The epoxy compound may be included in an amount of about 0.01 to about 20 parts by weight, e.g., about 0.1 to about 10 parts by weight based on 100 parts by weight of the photosensitive resin composition. When the epoxy compound is included within the ranges, close-contacting properties, storage properties, and the like may be improved.

In addition, the photosensitive resin composition may further include a silane coupling agent having a reactive substituent such as a carboxyl group, a methacryloyl group, an isocyanate group, an epoxy group, and the like to help improve its adherence to a substrate.

Examples of the silane-based coupling agent may include trimethoxysilyl benzoic acid, γ-methacryl oxypropyl trimethoxysilane, vinyl triacetoxysilane, vinyl trimethoxysilane, γ-iso cyanate propyl triethoxysilane, γ-glycidoxy propyl trimethoxysilane, β-(3,4-epoxycyclohexyl)ethyltrimethoxysilane, and the like. These may be used singularly or in a mixture of two or more.

The silane-coupling agent may be included in an amount of about 0.01 to about 10 parts by weight based on 100 parts by weight of the photosensitive resin composition. When the silane-coupling agent is included within the range, close-contacting properties, storing properties, and the like may be excellent.

In an implementation, the photosensitive resin composition may further include a surfactant in order to help improve coating properties and prevent a defect.

The surfactant may be a fluorine-based surfactant, and examples of the fluorine-based surfactant may include F-482, F-484, F-478, F-554, and the like of DIC Co., Ltd.

The surfactant may be used in an amount of about 0.001 to about 5 parts by weight based on 100 parts by weight of the photosensitive resin composition. When the surfactant is included within the ranges, excellent wetting on a glass substrate as well as coating uniformity may be secured, but a stain may not be produced.

In an implementation, the photosensitive resin composition may include other additives such as an antioxidant, a stabilizer, and the like in a predetermined amount provided that they do not deteriorate properties of the photosensitive resin composition.

According to an embodiment, a color filter manufactured using the photosensitive resin composition is provided.

A pattern-forming process in the color filter may be as follows.

The process may include coating the positive photosensitive resin composition on a support substrate in a method of spin coating, slit coating, inkjet printing, and the like; drying the coated positive photosensitive resin composition to form a photosensitive resin composition film; exposing the positive photosensitive resin composition film to light; developing the exposed positive photosensitive resin composition film in an alkali aqueous solution to obtain a photosensitive resin film; and heat-treating the photosensitive resin film.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS OF COMPOUNDS

Synthesis Example 1-1: Synthesis of Compound Represented by Chemical Formula 10-1

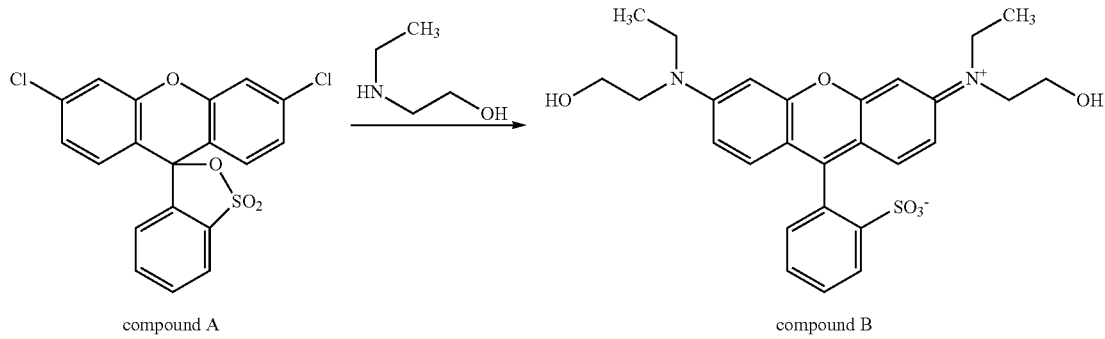

compound A  compound B

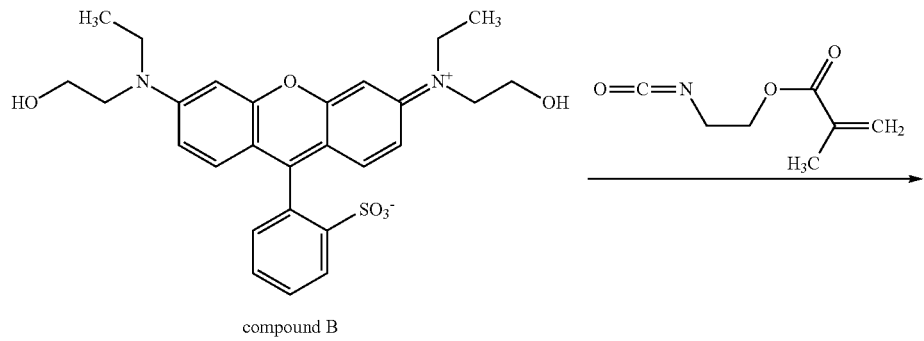

compound B

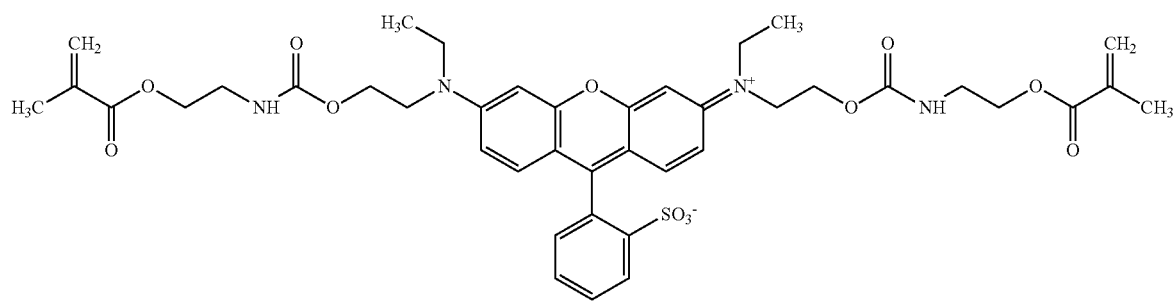

Chemical Formula 10-1

32 g of a compound A (CAS No. 77545-45-0) was put in a reactor and dissolved in 300 g of 2-propanol. Subsequently, 28.2 g of 2-ethylamino ethanol was added thereto, and the mixture was stirred at 80° C. for 8 hours. The reactant was cooled down, and 2 L of water was added thereto to produce a precipitate. The precipitate was suction-filtered and additionally washed with water. The filtered product was dried to obtain 32 g of a compound B (80% of a yield).

10 g of the compound B was put in a reactor, 30 g of dimethyl formamide and 7.0 g of metacryloyloxyethylisocyanate were added thereto, and the mixture was stirred for 8 hours. Subsequently, 100 g of dichloromethane was added to the reactant and the resultant was washed. Then, an organic layer therefrom was silica-filtered and distilled under a reduced pressure. The distilled mixture was dissolved in 10 g of dichloromethane, and the solution was added to 100 g of normal hexane in a dropwise fashion to produce a precipitate. The obtained precipitate was suction-filtered and additionally washed. The filtered product was dried to obtain 12.8 g of a compound represented by Chemical Formula 10-1 (80% of a yield).

MALDI-TOF MS: 820.3 m/z

Synthesis Example 1-2: Synthesis of Compound Represented by Chemical Formula 10-2

[Chemical Formula 10-2]

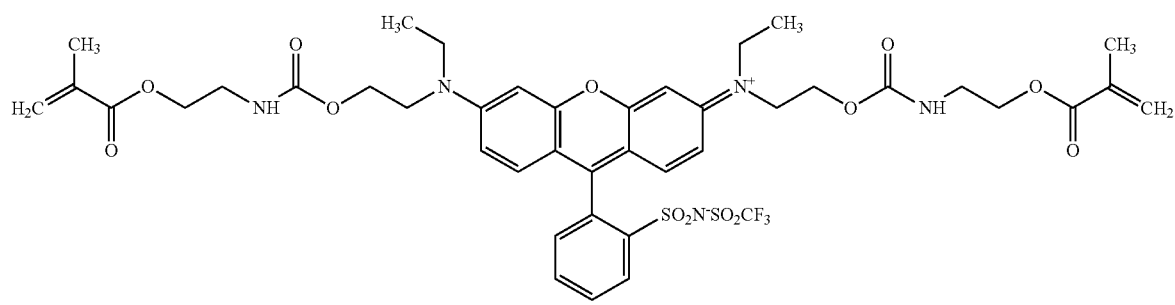

4.0 g of dimethyl formamide and 70 g of chloroform were put in a reactor and cooled and stirred at 0° C. 5.0 g of thionyl chloride was added in a dropwise fashion so that a liquid temperature of the mixture did not exceed 12° C. and the resultant was stirred at 0° C. for 30 minutes. 10 g of the compound represented by Chemical Formula 10-1 of Synthesis Example 1-1 was slowly added at ambient temperature, and then stirred at 35° C. for 3 hours. 0.6 g of thionyl chloride was added and the reaction solution was stirred at 35° C. for 1.5 hours.

The reaction solution was cooled again and 7.3 g of trifluoromethane sulfone amide was slowly added so that a temperature did not exceed 12° C., 12.3 g of triethyl amine was added in a dropwise fashion and the resultant was stirred at ambient temperature for 14 hours. Insoluble products was filtered and removed and a reaction solvent was removed under reduced pressure. 100 g of water was added, 15% sodium carbonate aqueous solution was added in a dropwise fashion, and suspension liquid was stirred for 1 hour while maintaining pH to be 7.0 to 7.5. The compound represented by Chemical Formula 10-2 was extracted using 100 g of dichloromethane, and column-purified using a dichloromethane/methanol 15/1 mixed solution. An organic solvent was removed and dried to obtain 7.1 g (61% yield) of the compound represented by Chemical Formula 10-2.

MALDI-TOF MS: 951.3 m/z

Synthesis Example 2-1: Synthesis of Compound Represented by Chemical Formula 11-1

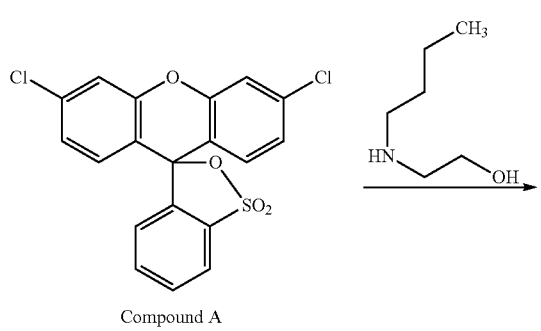

Compound A

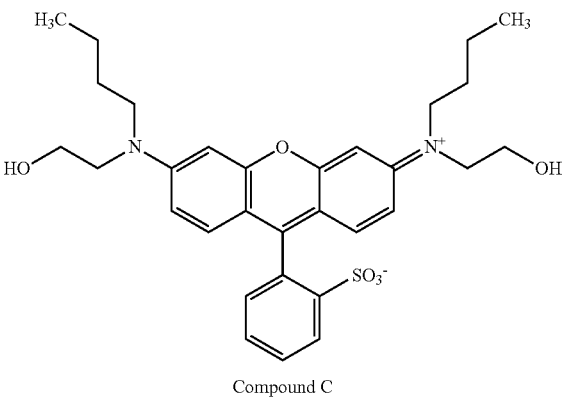

Compound C

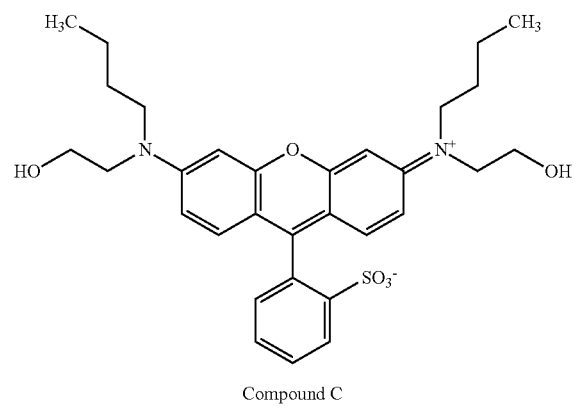

Compound C

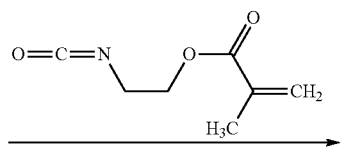

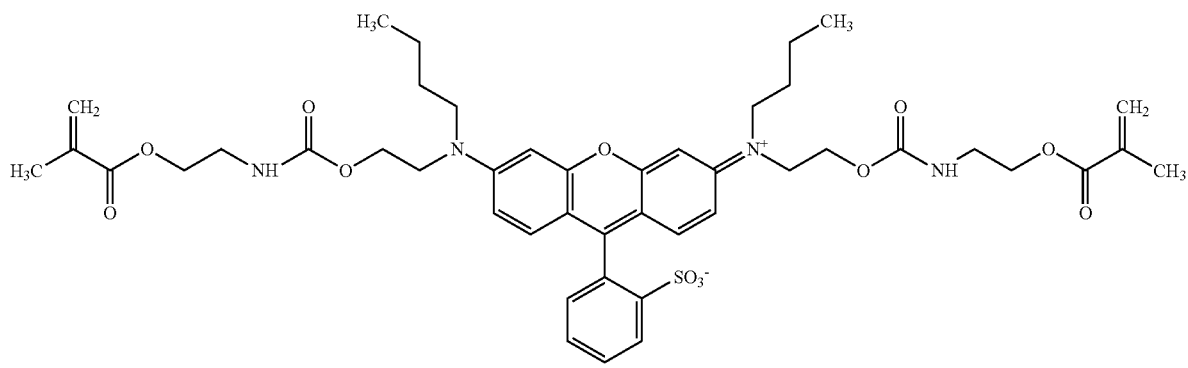

Chemical Formula 11-1

10 g of the compound A (CAS No. 77545-45-0) was put in a reactor and dissolved in 100 g of 2-propanol. Subsequently, 9.4 g of 2-butylamino ethanol was added thereto, and the mixture was stirred at 80° C. for 8 hours. The reactant was cooled down, and 800 mL of water was added thereto to produce a precipitate. The obtained precipitate was suction-filtered and additionally washed with water. The filtered product was dried to obtain 10.9 g of the compound C (78% of a yield). 10 g of the compound C was put in a reactor, 30 g of dimethyl formamide and 7.0 g of metacryloyloxyethylisocyanate were added thereto, and the mixture was stirred for 8 hours. 100 g of dichloromethane was added to the reactant and the resultant was washed. An organic layer obtained therefrom was silica-filtered and distilled under a reduced pressure. The distilled mixture was dissolved in 10 g of dichloromethane, and the solution was added to 100 g of normal hexane in a dropwise fashion to produce a precipitate. The obtained precipitate was suction-filtered and additionally washed. The filtered product was dried to obtain 11.6 g of a compound represented by Chemical Formula 11-1 (75% of a yield).

MALDI-TOF MS: 876.4 m/z

Synthesis Example 2-2: Synthesis of Compound Represented by Chemical Formula 11-2

[Chemical Formula 11-2]

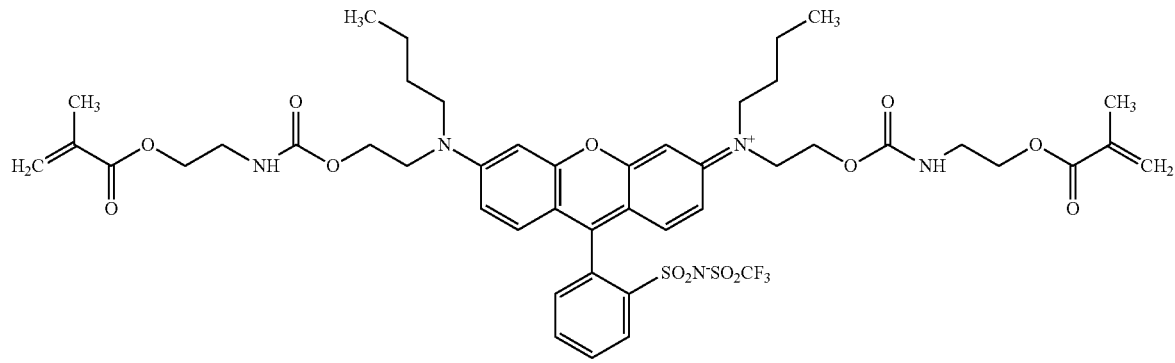

The compound represented by Chemical Formula 11-2 was synthesized by the same method as in Synthesis Example 1-2, except that a compound represented by Chemical Formula 11-1 was used instead of compound represented by Chemical Formula 10-1.

MALDI-TOF MS: 1007.3 m/z

Synthesis Example 3-1: Synthesis of Compound Represented by Chemical Formula 14-1

10 g of the compound B was put in a reactor, 30 g of dimethyl formamide and 6.4 g of acryloyloxyethylisocyanate were added thereto, and the mixture was stirred for 8 hours. 100 g of dichloromethane was added to the reactant and the resultant was washed. An organic layer obtained therefrom was silica-filtered and distilled under a reduced pressure. The distilled mixture was dissolved in 10 g of dichloromethane, and the solution was added to 100 g of normal hexane in a dropwise fashion to form a precipitate. The obtained precipitate was suction-filtered and additionally washed. The filtered product was dried to obtain 13.2 g of a compound represented by Chemical Formula 14-1 (85% of a yield).

[Chemical Formula 14-1]

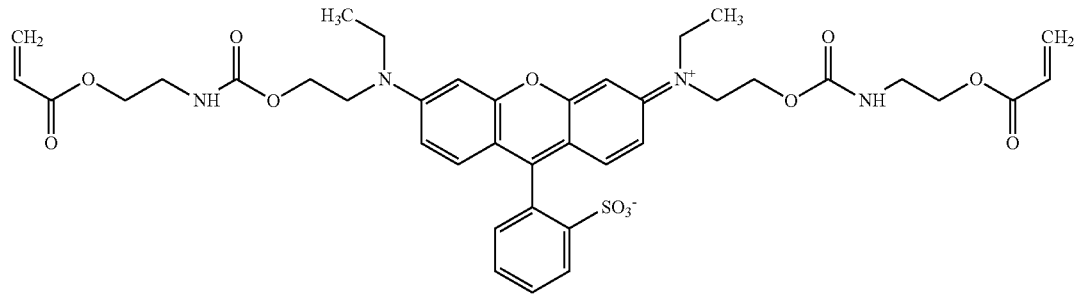

MALDI-TOF MS: 792.3 m/z

Synthesis Example 3-2: Synthesis of Compound Represented by Chemical Formula 14-2

[Chemical Formula 14-2]

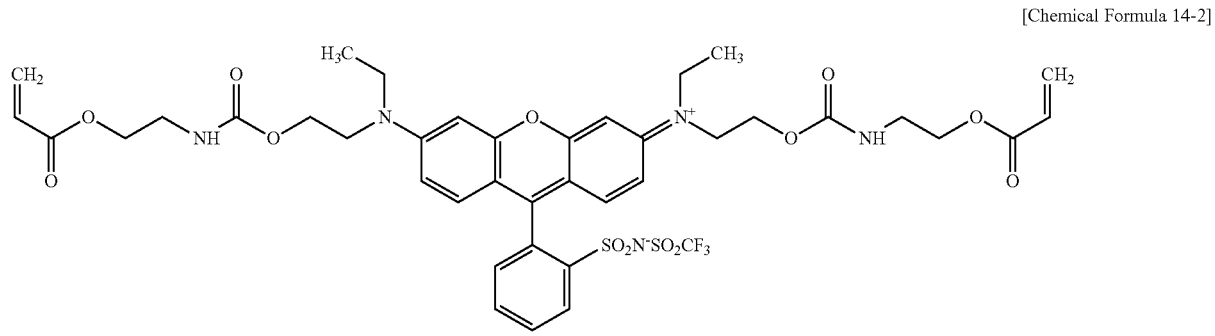

The compound represented by Chemical Formula 14-2 was synthesized by the same method as in Synthesis Example 1-2, except that a compound represented by Chemical Formula 14-1 was used instead of compound represented by Chemical Formula 10-1.
MALDI-TOF MS: 923.2 m/z Synthesis Example 4-1: Synthesis of Compound Represented by Chemical Formula 15-1

10 g of the compound B was put in a reactor, 30 g of dimethyl formamide and 9.1 g of 1-(1-isocyanato-1-methylethyl)-3-isopropylbenzene were added thereto, and the mixture was stirred for 8 hours. 100 g of dichloromethane was added to the reactant and the resultant was washed. An organic layer obtained therefrom was silica-filtered and distilled under a reduced pressure. The distilled mixture was dissolved in 10 g of dichloromethane, and the solution was added to 100 g of normal hexane in a dropwise fashion to form a precipitate. The obtained precipitate was suction-filtered and additionally washed. The filtered product was dried to obtain 12.1 g of a compound represented by Chemical Formula 15-1 (68% of a yield).

[Chemical Formula 15-1]

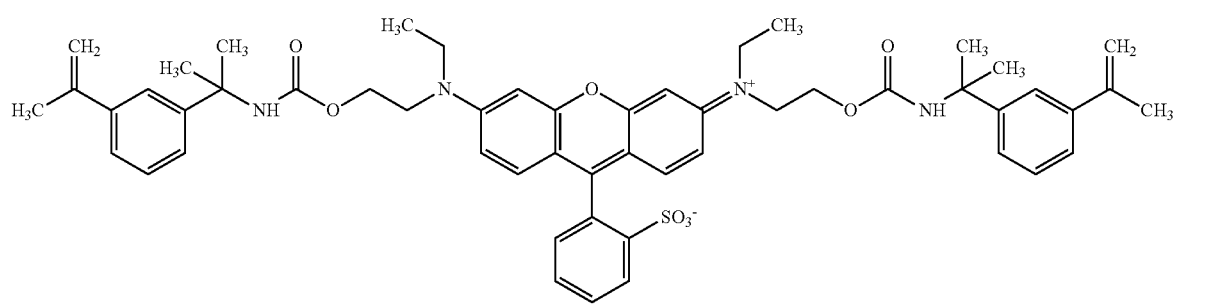

MALDI-TOF MS: 912.4 m/z

Synthesis Example 4-2: Synthesis of Compound Represented by Chemical Formula 15-2

[Chemical Formula 15-2]

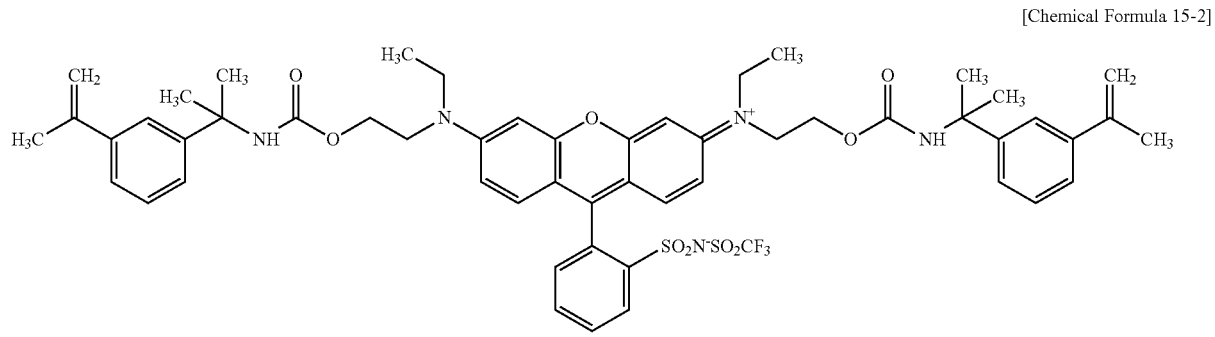

The compound represented by Chemical Formula 15-2 was synthesized by the same method as in Synthesis Example 1-2, except that a compound represented by Chemical. Formula 15-1 was used instead of compound represented by Chemical Formula 10-1.

MALDI-TOF MS: 1043.4 m/z

Synthesis Example 5-1: Synthesis of Compound Represented by Chemical Formula 17-1

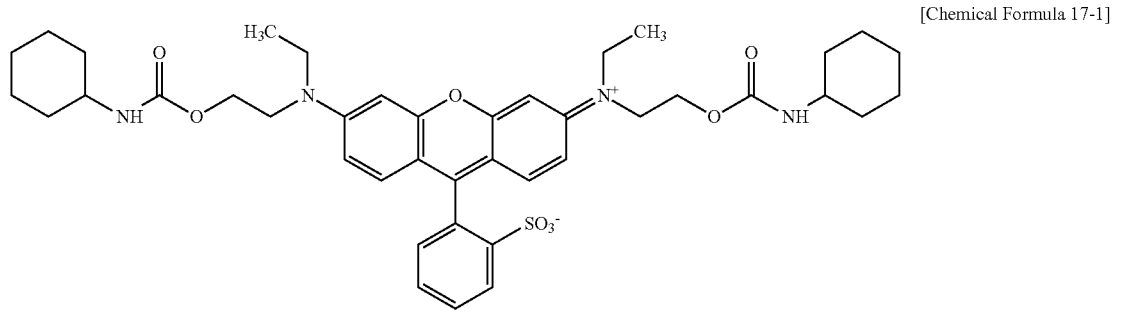

[Chemical Formula 17-1]

10 g of the compound B was put in a reactor, 30 g of dimethyl formamide and 6.7 g of cyclohexyl isocyanate were added thereto, and the mixture was stirred for 8 hours. 100 g of dichloromethane was added to the reactant and the resultant was washed.

An organic layer obtained therefrom was silica-filtered and distilled under a reduced pressure. The distilled mixture was dissolved in 10 g of dichloromethane, and the solution was added to 100 g of normal hexane in a dropwise fashion to form a precipitate. The obtained precipitate was suction-filtered and additionally washed. The filtered product was dried to obtain 12.7 g of a compound represented by Chemical Formula 17-1 (83% of a yield).
MALDI-TOF MS: 760.4 m/z Synthesis Example 5-2: Synthesis of Compound Represented by Chemical Formula 17-2

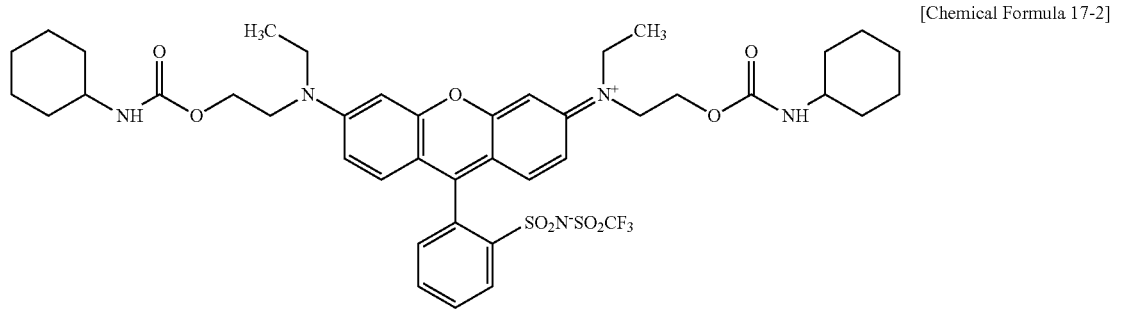

[Chemical Formula 17-2]

The compound represented by Chemical Formula 17-2 was synthesized by the same method as in Synthesis Example 1-2, except that a compound represented by Chemical Formula 17-1 was used instead of compound represented by Chemical Formula 10-1.
MALDI-TOF MS: 891.3 m/z Comparative Synthesis Example 1-1: Synthesis of Compound Represented by Chemical Formula X-1

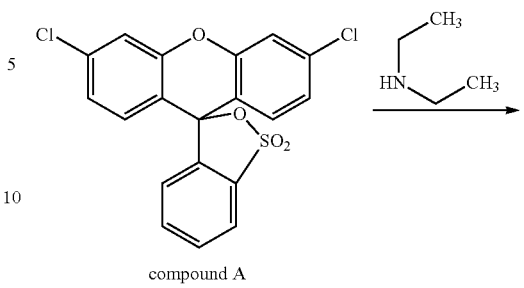

compound A

-continued

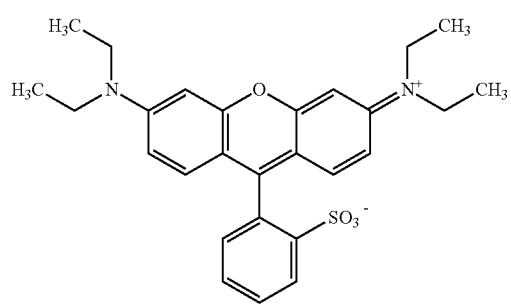

Chemical Formula X-1

10 g of the compound A (CAS No. 77545-45-0) was put in a reactor and dissolved in 100 g of 2-propanol. 7.2 g of diethylamine was added thereto, and the mixture was stirred at 80° C. for 8 hours. The reactant was cooled down, and 800 mL of water was added thereto to produce a precipitate. The obtained precipitate was suction-filtered and additionally washed with water. The filtered product was dried to obtain 9.9 g of a compound represented by Chemical Formula X-1 (84% of a yield).

MALDI-TOF MS: 478.2 m/z

Evaluation 1: Solubility Measurement

Dilution solvents (MeOH, CH$_2$Cl$_2$, cyclohexanone) were respectively added to 0.5 g of the compounds represented by Chemical Formula 6-1 to Chemical Formula 17-2 and the compound represented by Chemical Formula X-1, and each solution was stirred with Mixrotar VMR-5 (Iuchi Seieido Co., Ltd.) at 25° C. and 100 rpm for one hour. Dissolution states of the compounds (amounts of dissolved compounds) were shown in Table 1.

TABLE 1

| | Amount of dissolved compound (wt %) | | |
|---|---|---|---|
| | MeOH | CH$_2$Cl$_2$ | Cyclohexanone |
| Chemical Formula 6-1 | >10% | >10% | >3% |
| Chemical Formula 6-2 | >10% | >10% | >3% |
| Chemical Formula 7-1 | >10% | >10% | >3% |
| Chemical Formula 7-2 | >10% | >10% | >3% |
| Chemical Formula 8-1 | >10% | >10% | >3% |
| Chemical Formula 8-2 | >10% | >10% | >3% |
| Chemical Formula 9-1 | >10% | >10% | >1% |
| Chemical Formula 9-2 | >10% | >10% | >1% |
| Chemical Formula 10-1 | >10% | >10% | >5% |
| Chemical Formula 10-2 | >10% | >10% | >5% |
| Chemical Formula 11-1 | >10% | >10% | >5% |
| Chemical Formula 11-2 | >10% | >10% | >5% |
| Chemical Formula 12-1 | >10% | >10% | >5% |
| Chemical Formula 12-2 | >10% | >10% | >5% |
| Chemical Formula 13-1 | >10% | >10% | >3% |
| Chemical Formula 13-2 | >10% | >10% | >3% |
| Chemical Formula 14-1 | >10% | >10% | >5% |
| Chemical Formula 14-2 | >10% | >10% | >5% |
| Chemical Formula 15-1 | >10% | >10% | >5% |
| Chemical Formula 15-2 | >10% | >10% | >5% |
| Chemical Formula 16-1 | >10% | >10% | >1% |
| Chemical Formula 16-2 | >10% | >10% | >1% |
| Chemical Formula 17-1 | >10% | >10% | >3% |
| Chemical Formula 17-2 | >10% | >10% | >3% |
| Chemical Formula X-1 | >10% | <1% | <1% |

By way of summation and review, a pigment dispersion method is a method of forming a color filter that provides a colored thin film by repeating a series of processes such as coating a photopolymerizable composition including a colorant on a transparent substrate including a black matrix, exposing a formed pattern to light, removing a non-exposed part with a solvent, and thermally curing the same. A coloring photosensitive resin composition used for manufacturing a color filter according to the pigment dispersion method may include an alkali soluble resin, a photopolymerization monomer, a photopolymerization initiator, a solvent, other additives, and the like and additionally, an epoxy resin and the like. The pigment dispersion method may be applied to manufacture an LCD such as a mobile phone, a laptop, a monitor, and TV. The photosensitive resin composition for a color filter using the pigment dispersion method having many merits may have some drawbacks, e.g., there may be issues in minutely pulverizing of a powder, requiring various additives for stabilizing a dispersion liquid even if dispersed and complex processes, and further maintaining optimal quality of a pigment dispersion liquid under complicated storage and transportation conditions. In addition, a color filter manufactured by using a pigment-type photosensitive resin composition may have a limit in luminance and a contrast ratio due to a pigment particle size. Accordingly, a dye having similar heat resistance and chemical resistance to those of a pigment may be desirable.

The embodiments may provide a compound having improved solubility.

The compound according to an embodiment may have excellent solubility in an organic solvent, and thus a photosensitive resin composition including a colorant including the compound as a constituent element may be used to manufacture a color filter having excellent luminance, contrast ratio, and the like.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound represented by Chemical Formula 1:

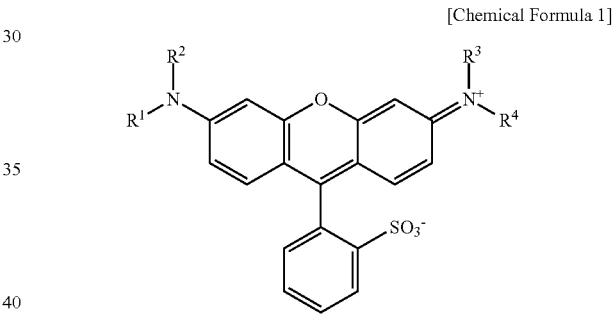

[Chemical Formula 1]

wherein, in Chemical Formula 1, $R^1$ to $R^4$ are each independently a substituted or unsubstituted C1 to C20 alkyl group, or a substituted or unsubstituted C6 to C20 aryl group, at least one of $R^1$ to $R^4$ being a group represented by Chemical Formula 2,

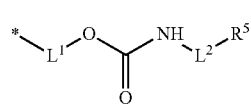

[Chemical Formula 2]

wherein, in Chemical Formula 2, $L^1$ is a substituted or unsubstituted C1 to C20 alkylene group, $L^2$ is a substituted or unsubstituted C1 to C20 alkylene group, a substituted or unsubstituted C3 to C20 cycloalkylene group, or a substituted or unsubstituted C0 to C20 arylene group, and $R^5$ is a substituent including an ethylenic unsaturated double bond, and wherein * is a bonding site.

2. The compound as claimed in claim 1, wherein $R^5$ is a substituted or unsubstituted acrylate group, a substituted or unsubstituted C2 to C20 alkenyl group, or a C6 to C20 aryl group including a substituent having an ethylenic unsaturated double bond at a terminal end thereof.

3. The compound as claimed in claim 1, wherein $R^5$ is a substituent represented by one of the following Chemical Formula 3 to Chemical Formula 5:

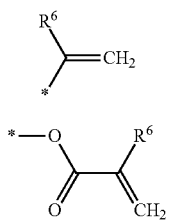
[Chemical Formula 3]

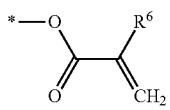
[Chemical Formula 4]

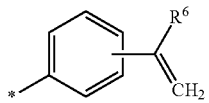
[Chemical Formula 5]

wherein, in Chemical Formulae 3 to 5,
$R^6$ is a hydrogen atom or a substituted or unsubstituted C1 to C5 alkyl group, and
* is a bonding site.

4. The compound as claimed in claim 1, wherein at least two of $R^1$ to $R^4$ are groups represented by Chemical Formula 2.

5. The compound as claimed in claim 1, wherein the compound represented by Chemical Formula 1 is a compound represented by one of Chemical Formula 6-1 15-1:

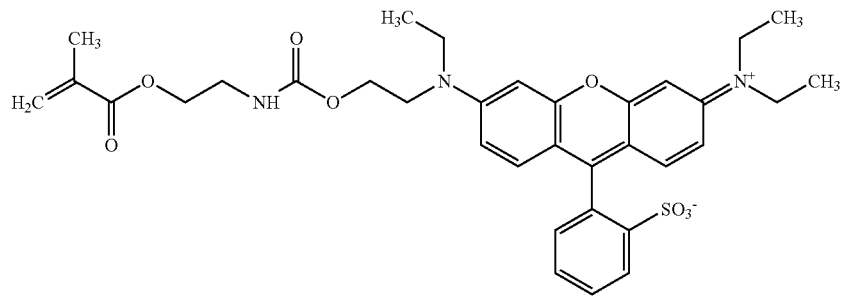
[Chemical Formula 6-1]

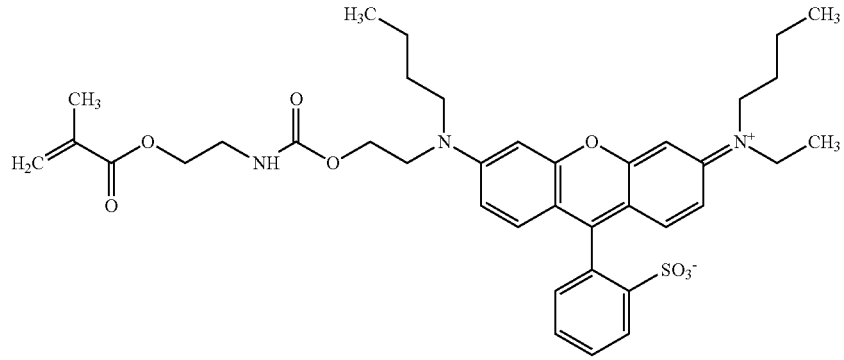
[Chemical Formula 7-1]

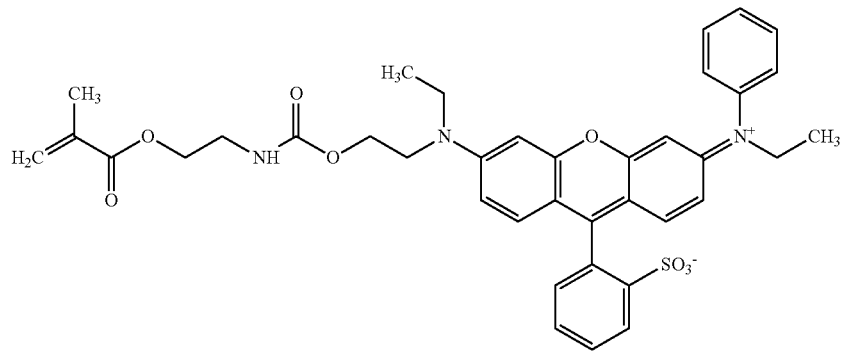
[Chemical Formula 8-1]

[Chemical Formula 9-1]
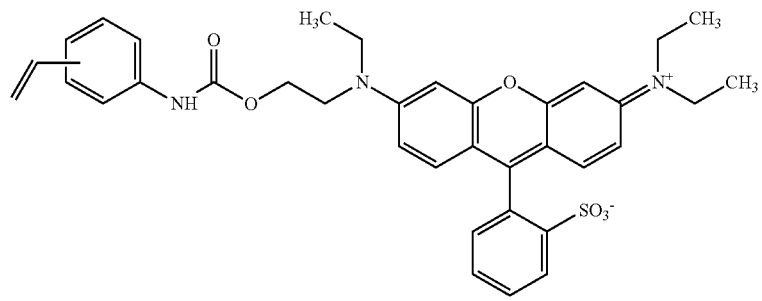
[Chemical Formula 10-1]
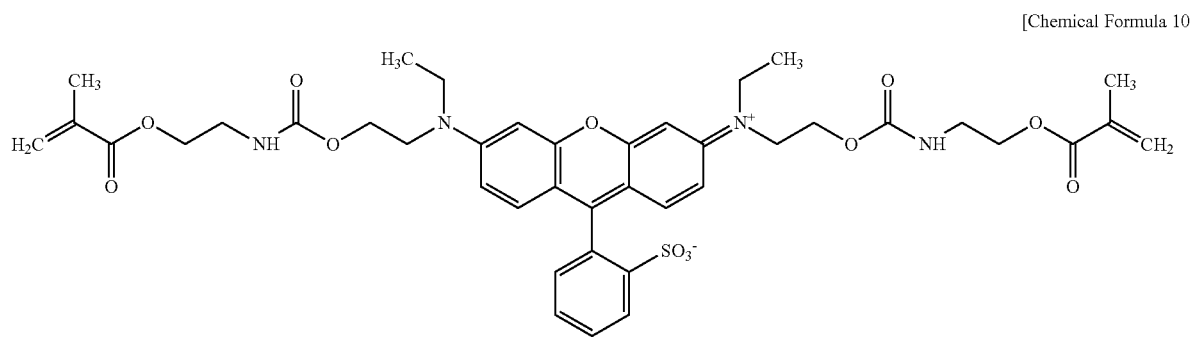
[Chemical Formula 11-1]
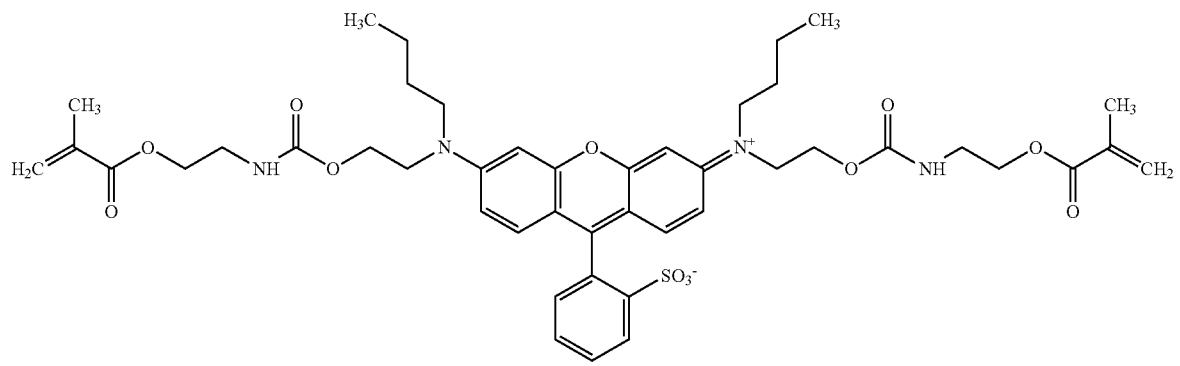
[Chemical Formula 12-1]
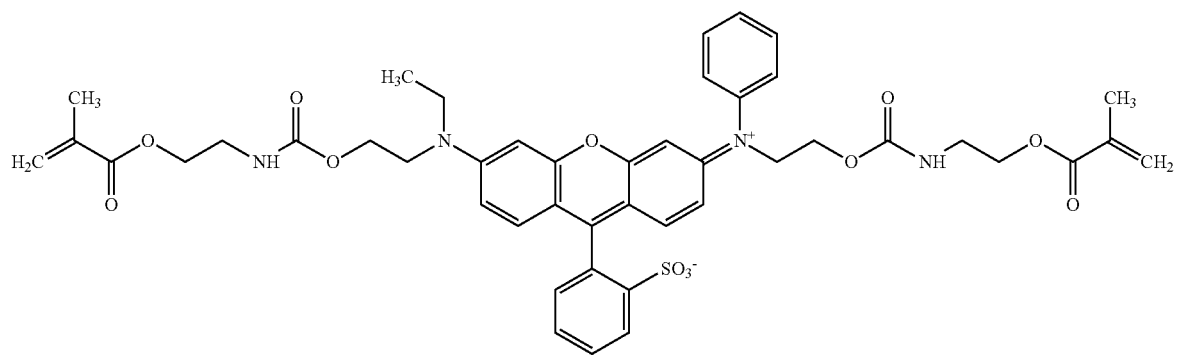

-continued

[Chemical Formula 13-1]

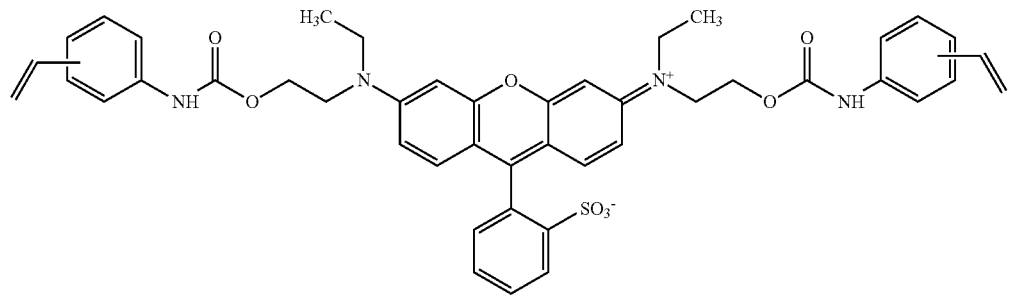

[Chemical Formula 14-1]

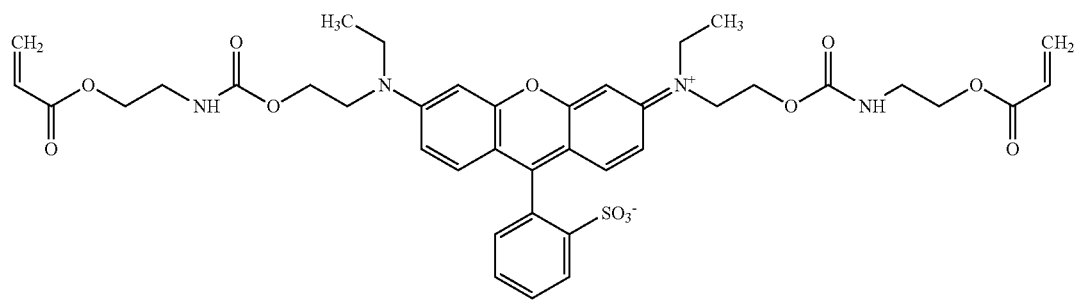

[Chemical Formula 15-1]

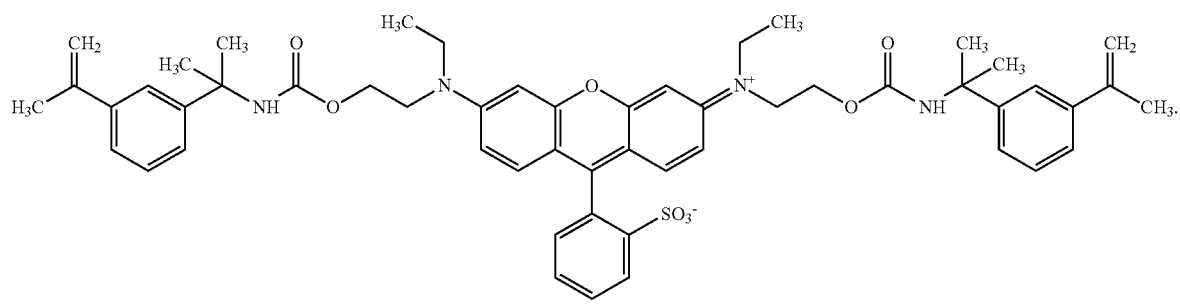

6. The compound as claimed in claim 1, wherein the compound represented by Chemical Formula 1 has maximum absorbance in a wavelength range of about 500 nm to about 600 nm.

7. An acrylic polymer formed by a copolymerization reaction of the compound as claimed in claim 1 with an ethylenic unsaturated monomer.

8. A photosensitive resin composition comprising the acrylic polymer as claimed in claim 7, wherein the acrylic polymer is a colorant.

9. A color filter manufactured using the photosensitive resin composition as claimed in claim 8.

10. A photosensitive resin composition comprising the compound as claimed in claim 1.

11. The photosensitive resin composition as claimed in claim 10, wherein the compound is a dye.

12. The photosensitive resin composition as claimed in claim 10, further comprising a binder resin, a photopolymerizable compound, a photopolymerization initiator, and a solvent.

13. A color filter manufactured using the photosensitive resin composition as claimed in claim 10.

14. A compound represented by Chemical Formula 1':

[Chemical Formula 1']

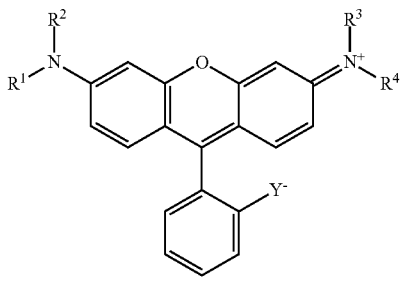

wherein, in Chemical Formula 1',
$R^1$ to $R^4$ are each independently a hydrogen, a substituted or unsubstituted C1 to C20 alkyl group, a substituted or unsubstituted C2 to C20 alkenyl group, a substituted or unsubstituted C3 to C20 cycloalkyl group, a substituted or unsubstituted C6 to C20 aryl group, a substituted or unsubstituted C2 to C20 heteroaryl group or a group represented by Chemical Formula 2, at least one of $R^1$ to $R^4$ being a group represented by Chemical Formula 2,

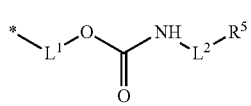
[Chemical Formula 2]

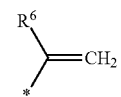
[Chemical Formula 3]

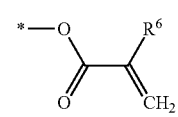
[Chemical Formula 4]

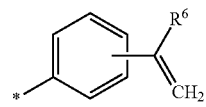
[Chemical Formula 5]

wherein, in Chemical Formula 2,
$L^1$ is a substituted or unsubstituted C1 to C20 alkylene group,
$L^2$ is a single bond, a substituted or unsubstituted C1 to C20 alkylene group, a substituted or unsubstituted C3 to C20 cycloalkylene group, or a substituted or unsubstituted C6 to C20 arylene group, and
$R^5$ is a substituted or unsubstituted C3 to C20 cycloalkyl group or a substituent including an ethylenic unsaturated double bond, and
Y is *—$SO_2NSO_2CF_3$, and
wherein * is a bonding site.

15. The compound as claimed in claim 14, wherein $R^5$ is the substituted or unsubstituted C3 to C20 cycloalkyl group, a substituted or unsubstituted acrylate group, a substituted or unsubstituted C2 to C20 alkenyl group, or a C6 to C20 aryl group including a substituent having an ethylenic unsaturated double bond at a terminal end thereof.

16. The compound as claimed in claim 14, wherein $R^5$ is an unsubstituted cyclohexyl group or a substituent represented by one of the following Chemical Formula 3 to Chemical Formula 5:

wherein, in Chemical Formulae 3 to 5,
$R^6$ is a hydrogen atom or a substituted or unsubstituted C1 to C5 alkyl group, and
* is a bonding site.

17. The compound as claimed in claim 14, wherein at least two of $R^1$ to $R^4$ are groups represented by Chemical Formula 2.

18. The compound as claimed in claim 14, wherein the compound represented by Chemical Formula 1' is a compound represented by one of Chemical Formula 6-2 to 17-2:

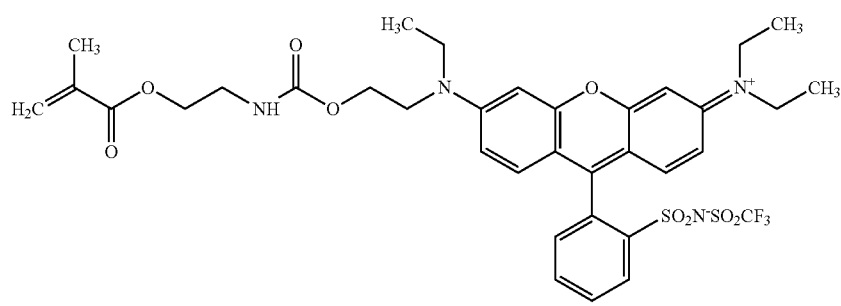
[Chemical Formula 6-2]

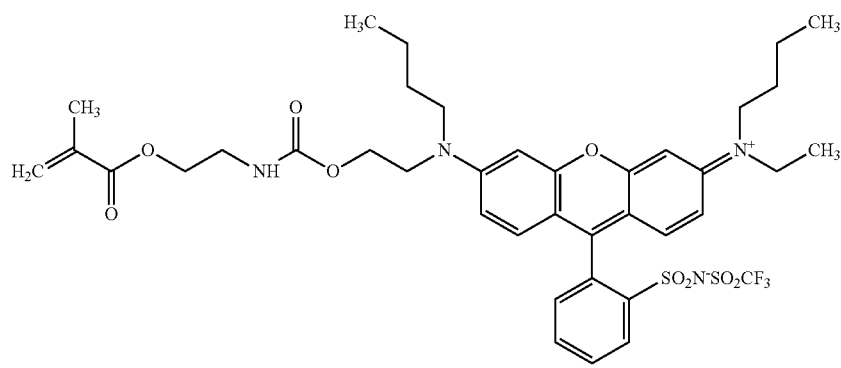
[Chemical Formula 7-2]

[Chemical Formula 8-2]
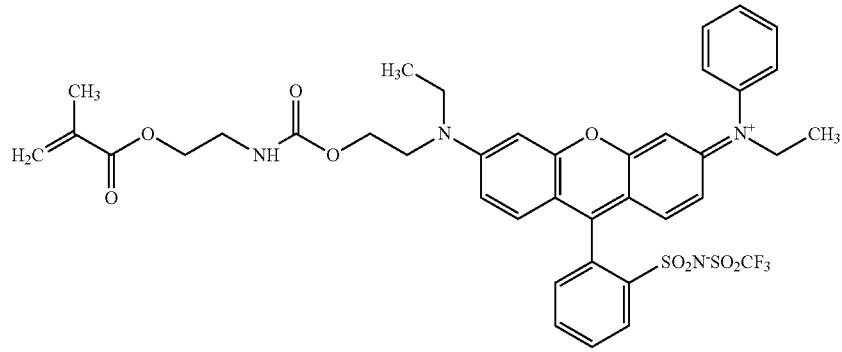
[Chemical Formula 9-2]
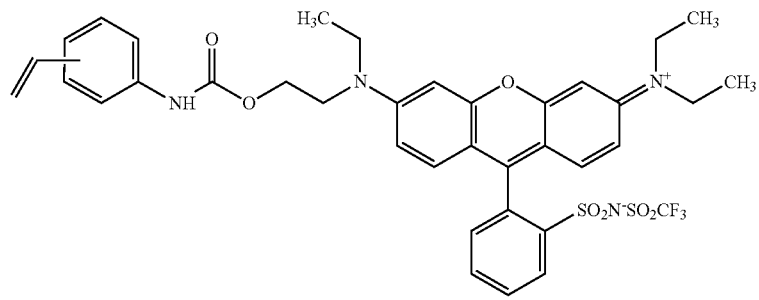
[Chemical Formula 10-2]
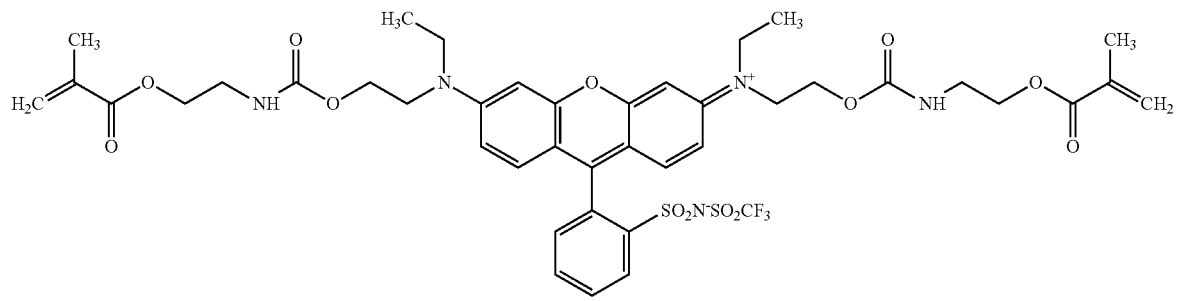
[Chemical Formula 11-2]
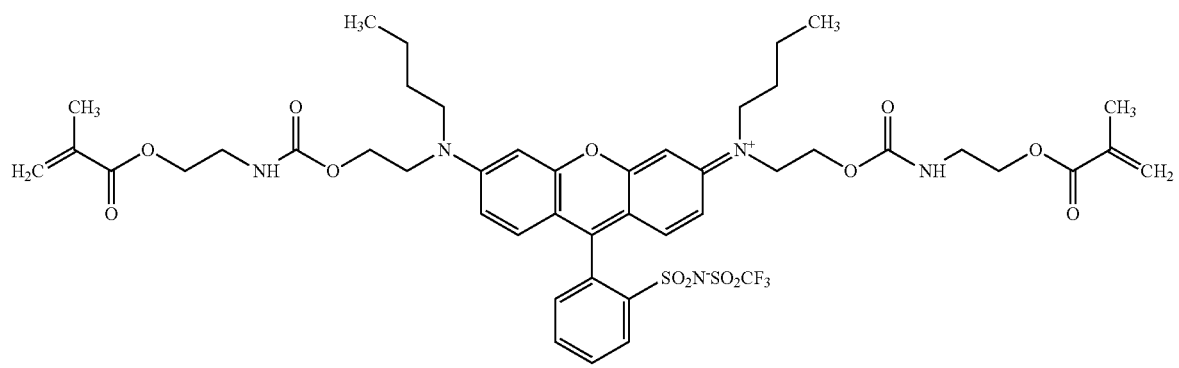

[Chemical Formula 12-2]
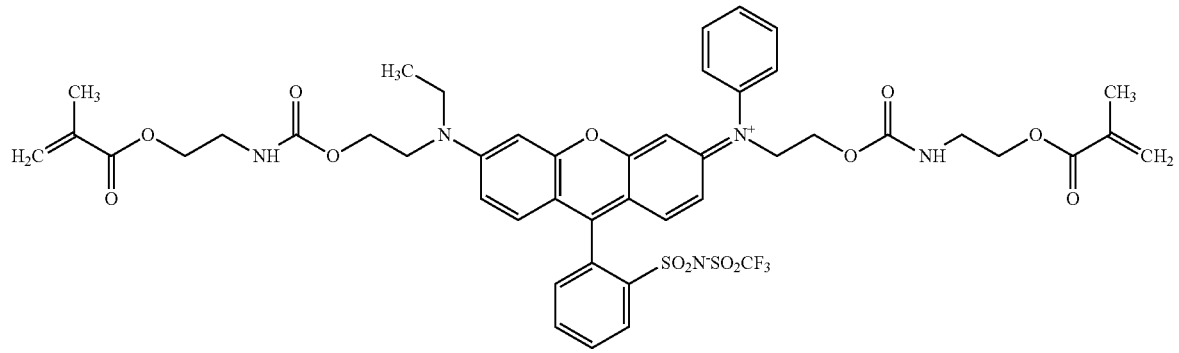
[Chemical Formula 13-2]
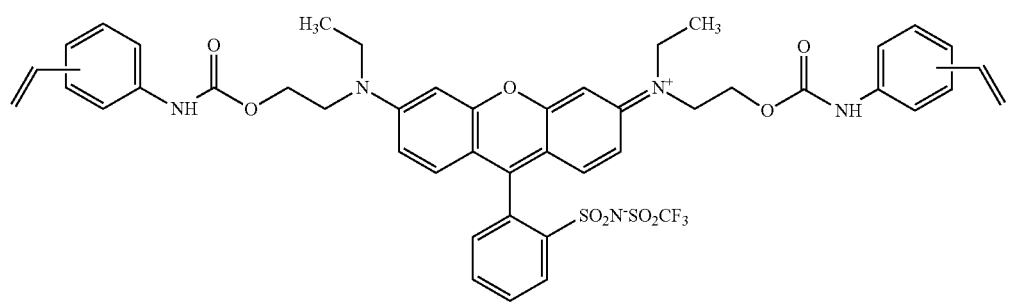
[Chemical Formula 14-2]
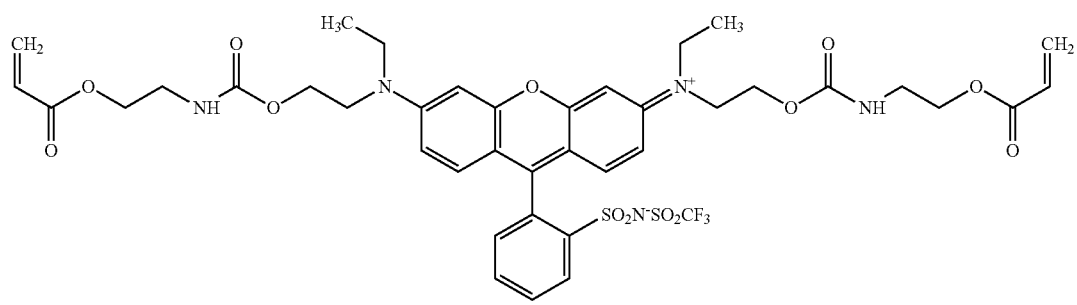
[Chemical Formula 15-2]
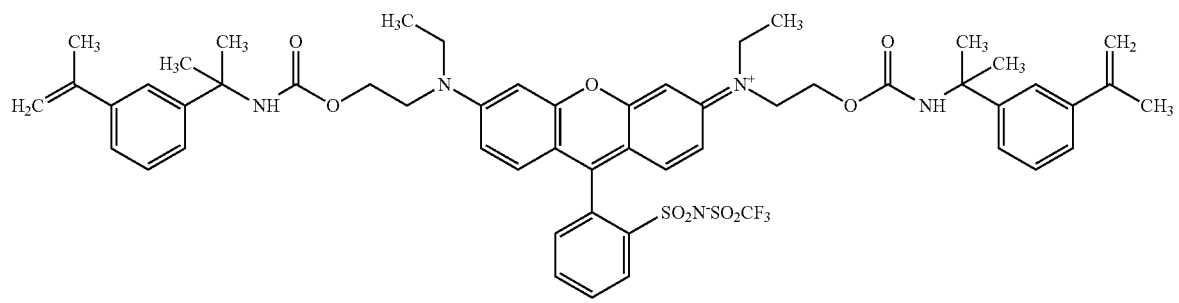
[Chemical Formula 16-2]
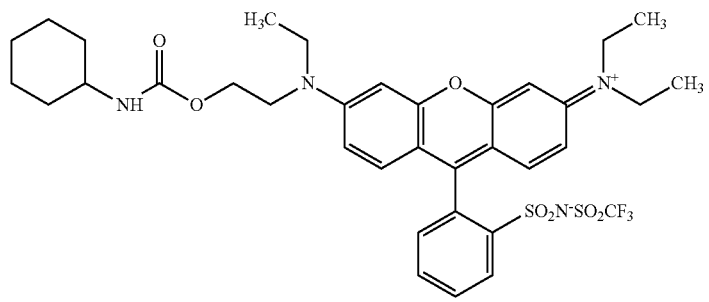

-continued

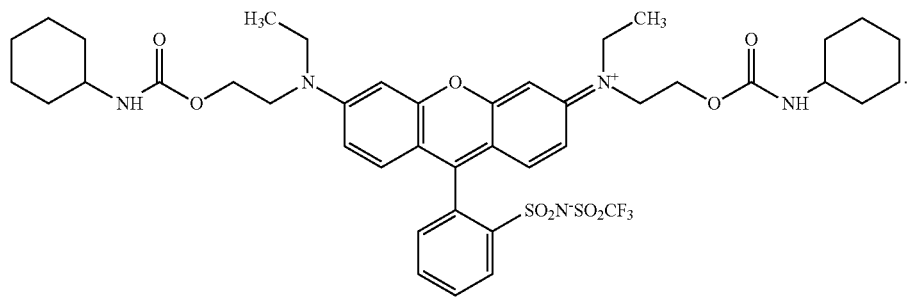

[Chemical Formula 17-2]

19. The compound as claimed in claim 14, wherein the compound represented by Chemical Formula 1' has maximum absorbance in a wavelength range of about 500 nm to about 600 nm.

20. An acrylic polymer formed by a copolymerization reaction of the compound represented by Chemical Formula 1' as claimed in claim 14 with an ethylenic unsaturated monomer.

21. A photosensitive resin composition comprising the acrylic polymer as claimed in claim 20, wherein the acrylic polymer is a colorant.

22. A color filter manufactured using the photosensitive resin composition as claimed in claim 21.

23. A photosensitive resin composition comprising the compound as claimed in claim 14.

24. The photosensitive resin composition as claimed in claim 23, wherein the compound is a dye.

25. The photosensitive resin composition as claimed in claim 23, further comprising a binder resin, a photopolymerizable compound, a photopolymerization initiator, and a solvent.

26. A color filter manufactured using the photosensitive resin composition as claimed in claim 23.

27. A compound represented by one of Chemical Formula 16-1 or 17-1:

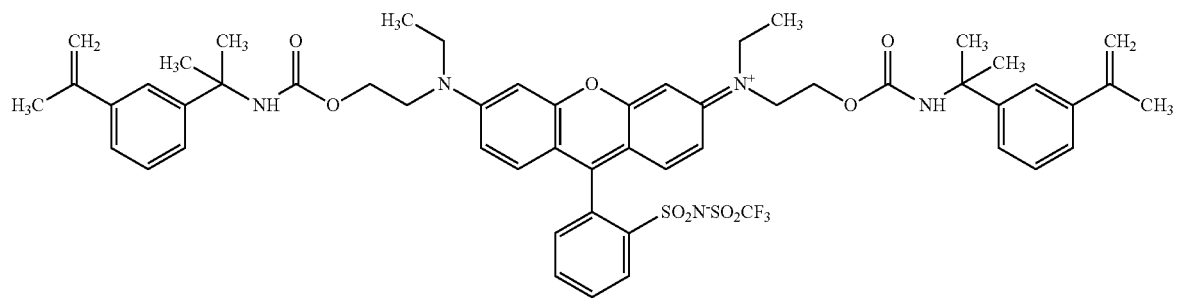

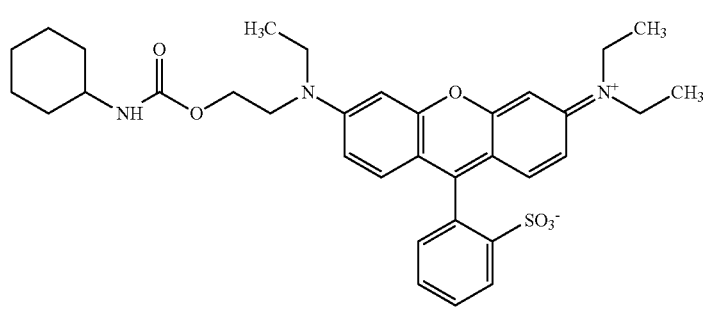

[Chemical Formula 16-1]

-continued
[Chemical Formula 17-1]
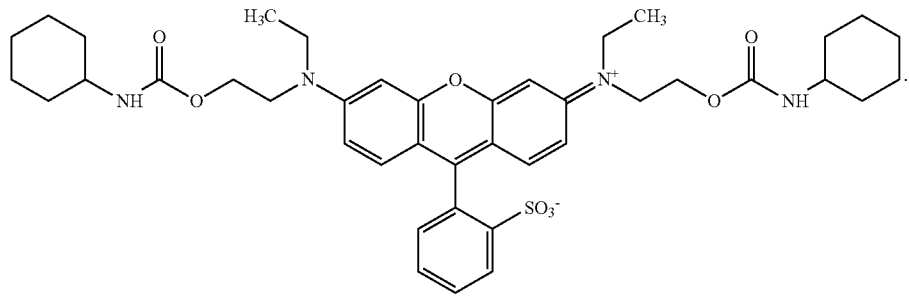
* * * * *